United States Patent
Ying et al.

(10) Patent No.: US 7,718,351 B2
(45) Date of Patent: May 18, 2010

(54) THREE-DIMENSIONAL FABRICATION OF BIOCOMPATIBLE STRUCTURES IN ANATOMICAL SHAPES AND DIMENSIONS FOR TISSUE ENGINEERING AND ORGAN REPLACEMENT

(75) Inventors: Jackie Y. Ying, Singapore (SG);
Shyi-Herng Kan, Singapore (SG);
Jeremy Loh Ming Hock, Singapore (SG); Karl Schumacher, Singapore (SG); James Tseng-Ming Hsieh, Singapore (SG)

(73) Assignee: Agency for Science, Technology & Research, Connexis (SG)

( * ) Notice: Subject to any disclaimer, the term of this patent is extended or adjusted under 35 U.S.C. 154(b) by 692 days.

(21) Appl. No.: 11/375,375

(22) Filed: Mar. 14, 2006

(65) Prior Publication Data
US 2007/0218544 A1    Sep. 20, 2007

(51) Int. Cl.
*G03F 1/00* (2006.01)

(52) U.S. Cl. .................. 430/322; 430/324; 430/270.1; 424/422; 424/423; 424/424; 623/23.64; 623/23.7; 623/23.71

(58) Field of Classification Search ...................... None
See application file for complete search history.

(56) References Cited

U.S. PATENT DOCUMENTS

| | | | | |
|---|---|---|---|---|
| 5,324,518 A | * | 6/1994 | Orth et al. ............... | 424/423 |
| 6,139,574 A | | 10/2000 | Vacanti et al. | |
| 6,176,874 B1 | | 1/2001 | Vacanti et al. | |
| 6,197,575 B1 | | 3/2001 | Griffith et al. | |
| 6,664,024 B1 | * | 12/2003 | Nguyen et al. ........... | 430/280.1 |
| 6,942,879 B2 | | 9/2005 | Humes | |
| 7,118,845 B2 | * | 10/2006 | DeVoe et al. ............. | 430/270.1 |
| 2002/0182241 A1 | | 12/2002 | Borenstein et al. | |
| 2003/0006534 A1 | | 1/2003 | Taboas et al. | |

(Continued)

FOREIGN PATENT DOCUMENTS

WO    WO 02/053193 A3    7/2002

(Continued)

OTHER PUBLICATIONS

"Contiguous." Merriam-Webster Online Dictionary. 2009. Merriam-Webster Online. Jun. 6, 2009 <http://www.merriam-webster.com/dictionary/contiguous>.*

(Continued)

*Primary Examiner*—Allison M. Ford
(74) *Attorney, Agent, or Firm*—Wolf, Greenfield & Sacks, P.C.

(57) ABSTRACT

Methods and apparatuses involving biocompatible structures for tissue engineering and organ replacement and, more specifically, biocompatible structures formed by three-dimensional fabrication, are described. In some embodiments, the biocompatible structures are scaffolds for cells that can be used as tissue engineering templates and/or as artificial organs. The structures may be three-dimensional and can mimic the shapes and dimensions of tissues and/or organs, including the microarchitecture and porosities of the tissues and organs. Pores in the structure may allow delivery of molecules across the structure, and may facilitate cell migration and/or generation of connective tissue between the structure and its host environment. Structures of the invention can be implanted into a mammal and/or may be used ex vivo as bioartificial assist devices.

24 Claims, 21 Drawing Sheets

U.S. PATENT DOCUMENTS

| | | | |
|---|---|---|---|
| 2003/0069718 | A1 | 4/2003 | Hollister et al. |
| 2004/0204760 | A1 | 10/2004 | Fitz et al. |
| 2004/0226620 | A1 | 11/2004 | Therriault et al. |
| 2005/0169962 | A1 | 8/2005 | Bhatia et al. |
| 2006/0024276 | A1* | 2/2006 | Ricordi ..................... 424/93.7 |

FOREIGN PATENT DOCUMENTS

WO    WO 2005/081970 A2    9/2005

OTHER PUBLICATIONS

Watson, A., et al., "Cyanoacrylate Tissue Adhesive for the Topical Approximation of Skin—Premarket Approval applications (PMAs) Guidance for Industry and FDA Staff", www.fda.gov/cdrh/ode/guidance/1233.html, Document notes original "issued on" date of Feb. 13, 2004.

Vozzi, G., et al., "Microsyringe Based Fabrication of High Resolution Organic Structures for Bioengineering Applications", IEEE (2000) pp. 141-145.

Sachlos, E., et al., "Making Tissue Engineering Scaffolds Work. Review on the Applications of Solid Freeform Fabrication Technology to the Production of Tissue Engineering Scaffolds", European Cells and Materials vol. 5 (2003) pp. 29-40.

Cumpston, B.H., et al., "Two-photon polymerization initiators for three-dimensional optical data storage and microfabrication", Nature, vol. 398 (1999) pp. 51-54.

Postnikova, B., et al., "Towards nanoscale three-dimensional fabrication using two-photon intiated polymerization and near-field excitation", Microelectronic Engineering 69 (2003) pp. 459-465.

Tormen, M., et al., "3D Patterning by means of nanoimprinting, X-ray and two-photon lithography", Microelectronic Engineering 73-74 (2004) pp. 535-541.

Keller, U., "Recent developments in compact ultrafast lasers", Nature, vol. 424 (2003) pp. 831-838.

Kawata, S., et al., "Finer features for functional microdevices, Micromachines can be created with higher resolution using two-photon absorption", Nature vol. 412 (2001) pp. 697-698.

Koike, N., et al., "Creation of long-lasting blood vessels", Nature, vol. 428 (2004) pp. 138-139.

Bhatia, S.N., et al., "Tissue Engineering at the Micro-Scale", Biomedical Devices 2:2, 131-144 (1999).

Chen, et al., "Tissue Engineering at the Micro-Scale", Biomedical Micro Devices, vol. 2:2 (1999) 131-144.

Filippidis, G., et al., "Construction of sub-micron three-dimensional structures employing multi-photon polymerization", The Third International Symposium on Nanomanufacturing, University of of Cyprus (2005).

Zhang, H., et al., "Microrobotics and MEMS-Based Fabrication Techniques for Scaffold-Based Tissue Engineering", Macromol. Biosci. (2005), 5, 477-489.

Basu, S., et al., "Properties of crosslinked protein matrices for tissue engineering applications synthesixed by multiphoton excitation", Journal of Biomedical Research Part A, vol, 71a, No. 2, Sep. 16, 2004, p. 359-368.

International Search Report, from PCT/US2007/006346, mailed May 3, 2007.

Yang, D., "Three-Dimensional Microfabrication by Two-Photon Lithography", Mts. Bulletin, vol. 30, Dec. 1, 2005, p. 976-982.

* cited by examiner

THREE-DIMENSIONAL FABRICATION OF BIOCOMPATIBLE STRUCTURES IN ANATOMICAL SHAPES AND DIMENSIONS FOR TISSUE ENGINEERING AND ORGAN REPLACEMENT

FIELD OF INVENTION

The present invention relates to methods and apparatuses involving biocompatible structures for tissue engineering and organ replacement and, more specifically, to methods and apparatuses involving biocompatible structures formed by three-dimensional fabrication for tissue engineering and organ replacement.

BACKGROUND

Tissue engineering and organ transplantation are principally concerned with the replacement of tissue and organs that have lost function due to injury or disease. In one approach toward this goal, organs are transplanted into a patient. However, the side effects of transplantation can be unpleasant, and can compromise the health of the organ recipient. In another approach, cells are cultured in vitro on biodegradable polymeric scaffolds to form tissues or neo organs that are then implanted into the body at the necessary anatomical site.

Several techniques have been proposed for forming scaffolds for tissue growth. For instance, U.S. Patent Publication No. 2002/0182241, entitled "Tissue Engineering of Three-Dimensional Vascularized Using Microfabricated Polymer Assembly Technology," by Borenstein et al., describes two-dimensional templates that are fabricated using high-resolution molding processes. These templates are then bonded to form three-dimensional scaffold structures with closed lumens. U.S. Pat. No. 6,176,874, entitled "Vascularized Tissue Regeneration Matrices Formed by Solid Free Form Fabrication Techniques," by Vacanti et al., describes solid free-form fabrication methods used to manufacture devices for allowing tissue regeneration and for seeding and implanting cells to form organ and structural components. U.S. Patent Publication No. 2003/0069718, entitled "Design Methodology for Tissue Engineering Scaffolds and Biomaterial Implants," by Hollister et al., describes anatomically shaped scaffold architectures with heterogeneous material properties, including interconnecting pores.

Despite the above efforts, significant developments in connection with many internal, physical structures, especially those of hollow and epithelial organs, has been limited, and improvements are needed.

SUMMARY OF THE INVENTION

Methods and apparatuses involving biocompatible structures for tissue engineering and organ replacement are described herein.

In one aspect, a series of articles for use as a template for cell growth are provided. The article comprises a structure comprising at least one wall defining a cavity, and a plurality of pores having a cross-sectional dimension of less than 40 microns formed in at least a portion of the wall and permeating the wall, thereby enabling exchange of a component between a portion interior to the cavity and a portion exterior to the cavity, wherein the structure is constructed and arranged for use as a template for cell growth.

In another embodiment, an article for use as a template for cell growth comprises a structure comprising at least one wall defining a cavity, the cavity having an inner diameter of less than 300 microns, and a plurality of pores formed in at least a portion of the wall and permeating the wall, thereby enabling exchange of a component between a portion interior to the cavity and a portion exterior to the cavity, wherein the structure is constructed and arranged for use as a template for cell growth.

In another aspect, a method for forming an article for use as a template for cell growth is provided. The method comprises using a multi-photon lithography process to form a structure comprising at least one wall defining a cavity, wherein the wall comprises a plurality of pores having a cross-sectional dimension of less than 40 microns in at least a portion of the wall and permeating the wall, thereby enabling exchange of a component between a portion interior to the cavity and a portion exterior to the cavity.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present inventors have realized the importance of addressing geometry, size, mechanical properties, and bioresponses in fabricating structures for tissue engineering and organ replacement, especially for structures involving hollow and epithelial organs. As such, the methods and apparatuses described herein have significant use in regenerative medicine.

The present invention relates to methods and apparatuses involving biocompatible structures for tissue engineering and organ replacement and, more specifically, to methods and apparatuses involving biocompatible structures formed by three-dimensional fabrication for tissue engineering and organ replacement. In some embodiments, the biocompatible structures are scaffolds for cells that can be used as tissue engineering templates and/or as artificial organs. The structures may be three-dimensional and can mimic the shapes and dimensions of tissues and/or organs, including the microarchitecture and porosities of the tissues and organs. For instance, certain embodiments of the invention can be fabricated to include very small features (e.g., less than 40 microns), such as small pore sizes, small cavities, and/or structures having thin walls. These features are particularly well-suited for structures involving hollow and epithelial organs. In some cases, a structure formed by three-dimensional fabrication comprises a wall defining a cavity and a plurality of pores in at least a portion of the wall. The pores may permeate the wall, at least at selected portions of the wall or all throughout the wall, and enable exchange of a component (e.g., a molecule and/or a cell) between a portion interior to the cavity and a portion exterior to the cavity. For instance, pores may allow delivery of molecules, cell migration, and/or generation of connective tissue between the structure and its host environment. Structures of the invention can be implanted into a mammal, or alternatively and/or additionally, can be used ex vivo as bioartificial assist devices.

Figure 1A:
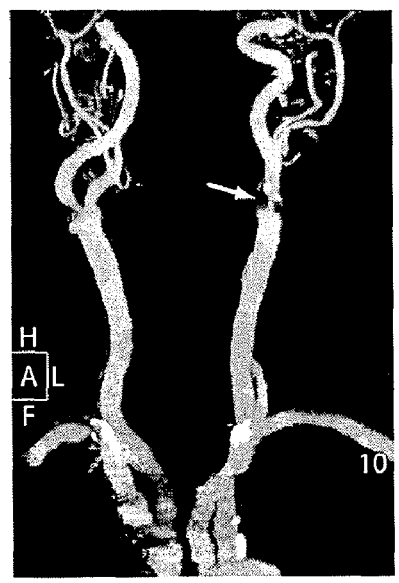
FIG. 1A is a high-resolution multi-section computed tomography scan of a bilateral carotid artery stenosis (prior art)
Figure 1B:
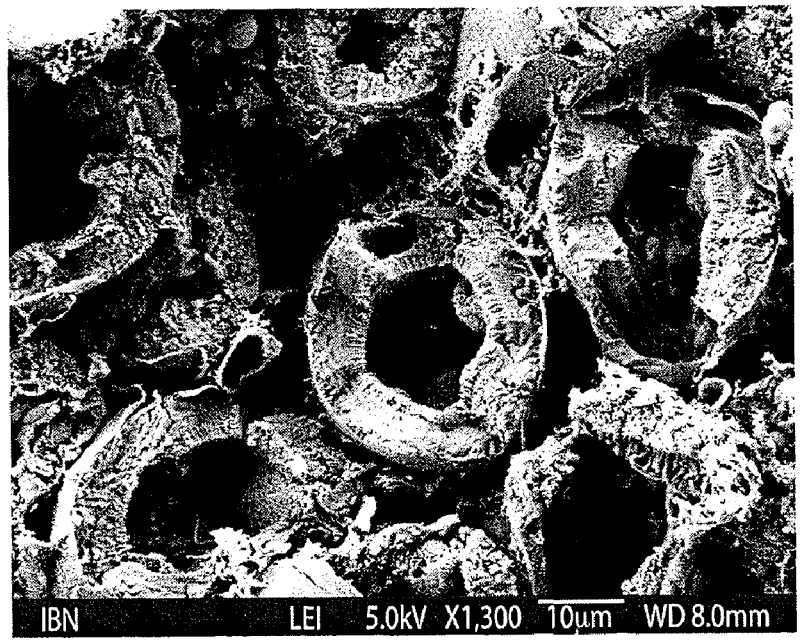
FIG. 1B is an SEM image showing a cross section of a mouse kidney proximal tubule (prior art)

In some embodiments, structures for tissue engineering and/or organ replacement can be drawn, imaged, and/or scanned using a variety of tools, including computer-aided design (CAD) tools, high-resolution multi-section computed tomography (CT) scans (FIG. 1), and/or three-dimensional scanners. For instance, FIG. 1 shows a CT scan of a bilateral carotid artery stenosis, showing severe stenosis of the left internal carotid artery, as shown by the arrow. This and other image files can be converted into a proper file format, and fed into systems that can produce the structures. A variety of techniques can be used to form structures as described herein. These methods can, in some cases, control compositions and micro-architectures of the structures. Appropriate systems and techniques for fabricating structures for tissue engineering and/or organ replacement include, but are not limited to, three-dimensional printing (e.g., three-dimensional layering), multi-photon lithography, stereolithography (SLA), selective laser sintering (SLS) or laser ablation, ballistic particle manufacturing (BPM), and fusion deposition modeling (FDM). In certain preferred embodiments, structures are formed by three-dimensional printing or multi-photon lithography techniques. Other techniques for fabricating structures for tissue engineering and/or organ replacement can also be used.

In one embodiment, a three-dimensional printing technique is used to fabricate such structures. The three-dimensional printing technique may include the use of a tool such as the Eden 260 Rapid Prototyping Tool (RPT). The Eden 260 RPT is a polymer dispensing system that can print droplets of polymer precursor (e.g., a build material) and sacrificial material using a piezoelectric-actuated nozzle. Using such tools, a three-dimensional image file can be processed and the image may be sliced into many layers. Each layer can then printed on top of each other, and the polymer precursor can be polymerized.

Figure 2A:
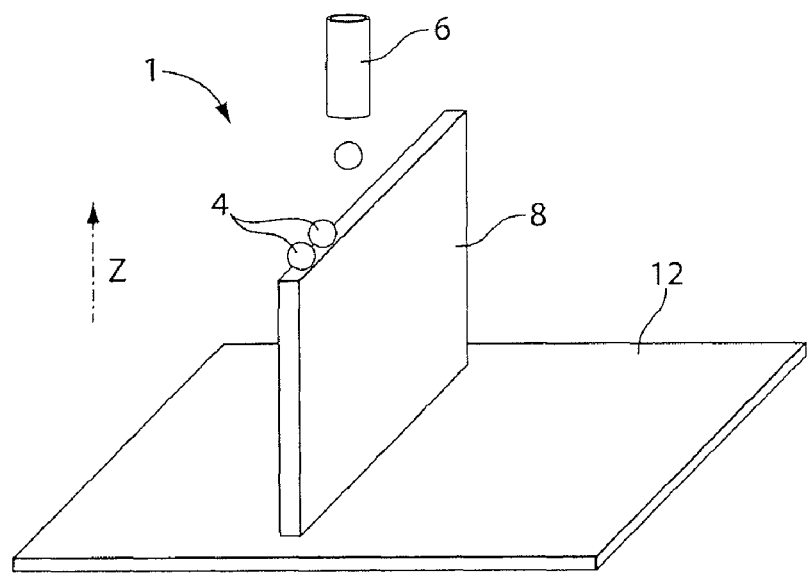
FIGS. 2A and 2B show schematic diagrams of horizontal and vertical three-dimensional printing techniques, respectively, according to one embodiment of the invention.
Figure 2B:
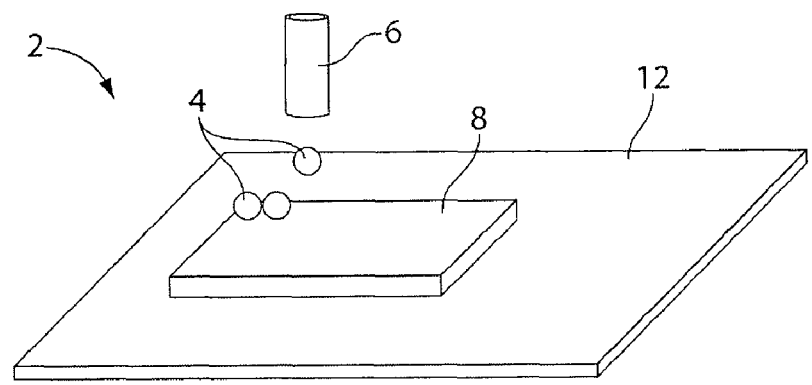

In the embodiment illustrated in FIGS. 2A and 2B, tools 1 and 2 dispense droplets 4 of different materials using one or more nozzles 6. Droplets 4 may be printed to form structure 8, supported by substrate holder 12. As shown in FIG. 2A, structure 8 can be formed by a vertical printing process; FIG. 2B shows horizontal printing of structure 8.

A first material to be printed may include, for instance, a build material comprising a UV cross linkable polymer that is not soluble in a basic solution, which may be used to print the structure. Open areas (e.g., pores) in the design may be filled with a second material, i.e., a sacrificial material, that is not UV cross linkable material but that is soluble in a basic solution. The first and second materials can be dispensed droplet by droplet and layer by layer. After each layer of material have been dispensed, a roller may be used to smooth out the surface and the material may be polymerized. This process may be repeated until the structure is built, and the sacrificial layer may then be removed. Resolutions of the structures formed by such a process may be limited by the dispensed droplet size and/or the print direction (i.e., vertical or horizontal printing), as discussed in more detail below. In some particular embodiments, after droplets have been dispensed and rolled, the average feature size may be about 42 $\mu m \times 84\ \mu m \times 16\ \mu m$.

Different methods of polymerization are possible, including polymerization by UV radiation and by heat, which may depend on the particular material used. In one particular embodiment, an image file of an organ can be printed in three dimensions in a polymer, e.g., EDEN Fullcure 720 polymer, to form a structure. Other three-dimensional fabrication tools can also be used to fabricate structures using this approach.

Figure 3:
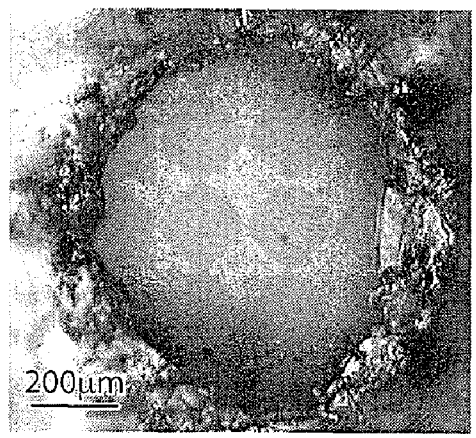
FIG. 3 shows a pore fabricated using the fabrication techniques shown in FIGS. 2A and 2B according to another embodiment of invention.
Figure 4:
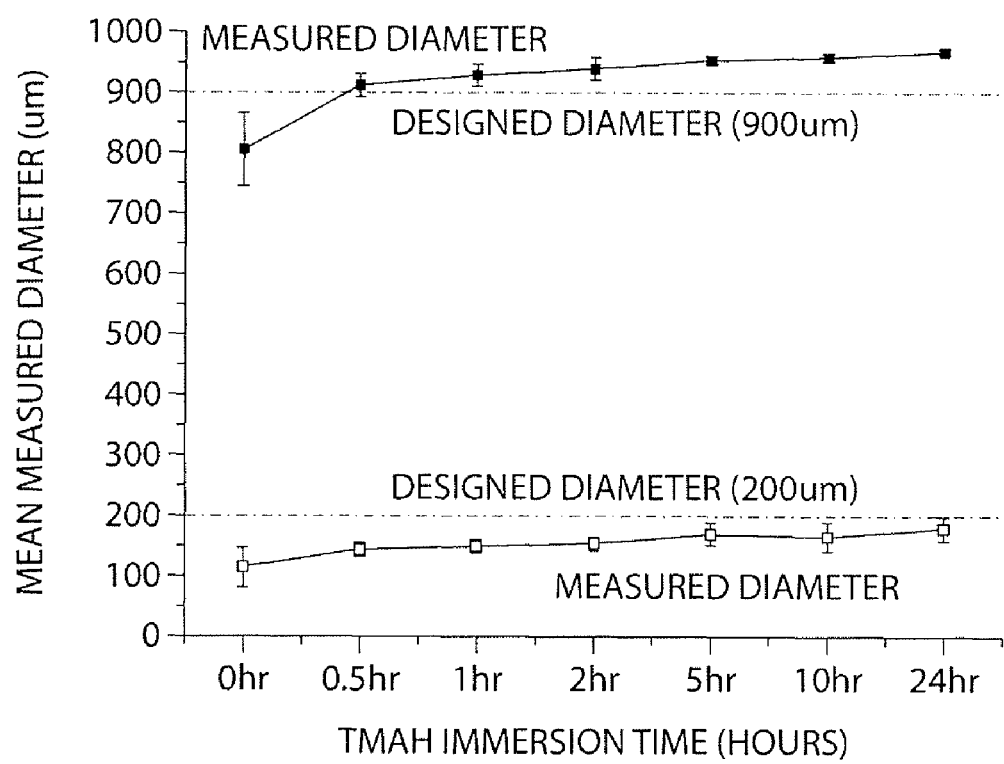
FIG. 4 shows a plot characterizing pores fabricated using the techniques shown in FIGS. 2A and 2B according to another embodiment of invention.

If desired, arrays of holes or pores can be drawn onto a scanned image to form a porous skeleton of the imaged tissue or organ. In other words, the pores can be fabricated using the same fabrication technique used to form the structure. FIG. 3 shows one example of a pore fabricated using the Eden 260 RPT. FIG. 4 shows characterization of certain pores fabricated using this tool.

A structure may also comprise holes or pores throughout, or within certain regions, of the structure, as described below. In some instances, pores having a cross-sectional dimension of less than or equal to 1 mm, less than or equal to 100 microns, less than or equal to 50 microns, less than or equal to 40 microns, less than or equal to 30 microns, less than or equal to 10 microns, less than or equal to 5 microns, less than or equal to 1 micron, or less than or equal to 100 nm can be formed in a structure by a suitable printing technique. In some embodiments, more than one technique for introducing porosity in a structure can be used. For instance, porosity can be induced in a structure by methods such as solution casting, emulsion casting, polymer blending, and phase transition induced porosity, as described in more detail below.

In some embodiments, structures for tissue engineering and/or organ replacement are formed using a multi-photon lithography system. For instance, two-photon lithography or three-photon lithography systems may be used. Multi-photon polymerization may involve the use of an ultra-fast infrared laser (e.g., a femtosecond laser operating at a wavelength of 1028 nm), which can be focused into the volume of a photo-sensitive material. The polymerization process can be initiated by non-linear absorption within the focal volume. By moving the focused laser three-dimensionally through the resin, three-dimensional structures can be fabricated.

In one embodiment, a two-photon lithography system can be used to fabricate structures for tissue engineering and/or organ replacement. In a two-photon lithography system, a monomer mixed with a photo initiator that absorbs UV light may be exposed to an infra-red laser. Two photons of infra red light can be absorbed by the resin/chemicals and a single photon of ultra-violet light can be released. The released photon can then be absorbed by the photo initiator to produce free radicals which can cause polymerization of the monomers. Since the two-photon absorption cross-section is very small, for the release of sufficient UV light to induce free radical polymerization in the chemicals, a large amount of energy (terawatt) can be delivered to the chemical by the laser. This energy density could be generated at the focal point of a laser beam from an ultra-fast (e.g., femtosecond) pulse laser. Two-photon-absorption only occurs at the focal point of the beam and not at the laser beam path, hence a very small volume (e.g., femtoliter) of monomer can be polymerized through the release of free radicals from the photo initiator. After the structure has been polymerized, e.g., from a block of resin or in a petri dish of monomer, the unexposed chemicals can be washed away with a suitable solvent, leaving behind the final structure. The technique can been used with a variety of materials, including acrylate and epoxy polymers such as ethoxylated trimethylolpropane triacrylate ester and alkoxylated trifunctional acrylate ester, as described in more detail below. This system can be used, for instance, when structures with fine resolution are desired. I.e., in some cases, multi-photon lithography can be used to form structures having submicron (e.g., less than one micron) resolution.

Two-photon lithography offers the ability to fabricate high resolution three-dimensional devices, sometimes in three process steps. Compared with traditional 2D micro-fabrication techniques, where multiple mask layers may be required to build complex three-dimensional devices, the two-photon lithography system may have a very simple setup. However, in some instances, the process of fabricating such devices is a serial process and device fabrication may be slow, taking up to 13 mins for a 10 $\mu m \times 10\ \mu m \times 10\ \mu m$ device. In order to build scaffolds of any significant volume would require days of scanning, this being unrealistic for many commercial applications. Significant upgrades to the two-photon system, compared to systems described by others, can be made, as discussed in the Examples.

Figure 5:
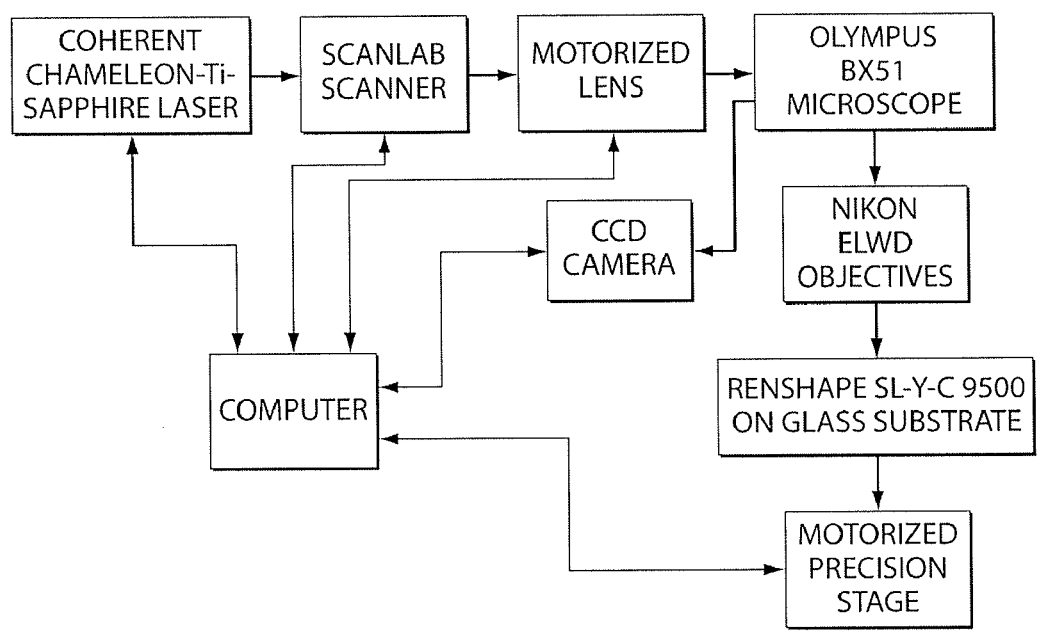
FIG. 5 shows a flow chart of a two-photon lithography system according to another embodiment of invention.
Figure 6:
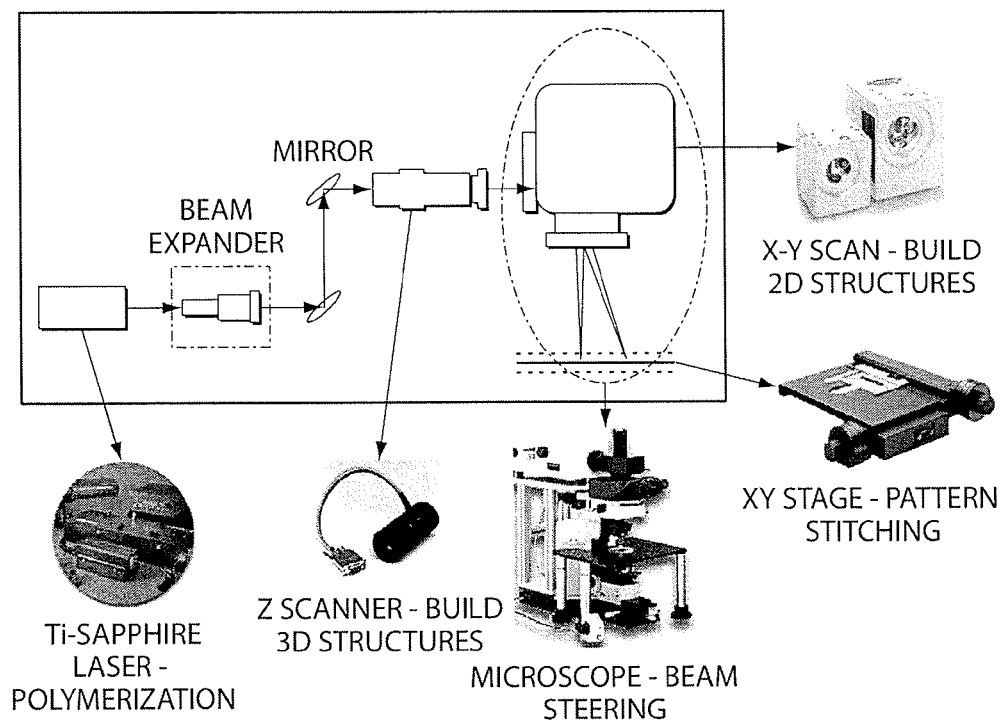
FIG. 6 shows one example of an experimental setup of a two-photon lithography system according to another embodiment of invention.

FIG. 5 shows a flow chart of a two-photon lithography system and FIG. 6 illustrates an example of an experimental setup of such a system. FIGS. 7A-7D show examples of various structures that can be fabricated using a two-photon lithography system, as described in more detail in the Examples.

In one embodiment, stereolithography can be used to form structures for tissue engineering and/or organ replacement. Stereolithography may involve the use of a focused ultra-violet laser scanned over the top of a reservoir containing a photopolymerizable liquid polymer. The UV laser can cause the polymer to polymerize where the laser beam strikes the surface of the reservoir, resulting in the formation of a solid polymer layer at the surface of the liquid. The solid layer can be lowered into the reservoir and the process can repeated for formation of the next layer, until a plurality of superimposed layers of the desired structure is obtained.

In another embodiment, selective laser sintering (or laser ablation) can be used to form structures for tissue engineering and/or organ replacement. Selective laser sintering may involve the use of a focused laser beam to sinter areas of a loosely-compacted plastic powder, where the powder is applied layer by layer. For instance, a thin layer of powder can be spread evenly onto a flat surface, i.e., using a roller mechanism. The powder can be raster-scanned using a high-power laser beam. The areas of the powder material where the laser beam was focused can be fused, while the other areas of powder can remain dissociated. Successive layers of powder can be deposited and raster-scanned, one on top of another, until an desired structure is obtained. In this process, each layer can be sintered deeply enough to bond it to the preceding layer.

In some embodiments involving three-dimensional fabrication, variation of the laser intensity and/or traversal speed can be used to vary the crosslinking density within a structure. In some cases, this allows the properties of the material to be varied from position to position with the structure. Variation of the laser intensity and/or traversal speed can also control the degree of local densification within the material. For instance, regions where the laser intensity is high or the traversal speed is low can create areas of higher density.

Structures used as templates for cell growth can be formed in organic and/or inorganic materials including polymers, ceramics, gels, and glass, as described in more detail below. Surface properties of the structures can be modified by various techniques. In some cases, surfaces of a structure can be modified by coating and/or printing an additive proximate the structure. In other cases, additives can be incorporated into the material used to form the structure (i.e., embedded in the structure during fabrication), as described in more detail below. Surfaces may be modified with additives such as proteins and/or other suitable surface-modifying substances. For example, collagen, fibronectin, an RGD peptide, and/or other extracellular matrix (ECM) proteins or growth factors can be coated onto the structure, i.e., to elicit an appropriate biological response from cells, including cell attachment, migration, proliferation, differentiation, and gene expression. Cells can then be seeded onto surfaces of this structure. In one embodiment, cell adhesion proteins can be incorporated into certain channels and/or pores of a structure to facilitate ingrowth of blood vessels in these channels and/or pores. In another embodiment, growth factors can be incorporated into the structure to induce optimal cell growth conditions that triggers healthy tissue formation within certain regions of the structure.

In some cases, it may be desirable to modify all or portions of a surface with a material that inhibits cell adhesion, such as a surfactant (e.g., polyethylene glycol and polypropylene oxide-polyethylene oxide block copolymers). For instance, areas of a structure where it is not desirable for cellular growth can be coated with such materials, i.e., to prevent excessive soft connective tissue ingrowth into the structure from the surrounding tissue. In some cases, modification of surface properties of the structure can be used to position cells at specific sites within the structure. In some embodiments, a combination of cell-adhering and cell-inhibiting substances can be incorporated into various portions of a structure to simultaneously facilitate and inhibit cell growth, respectively.

Figure 8A:
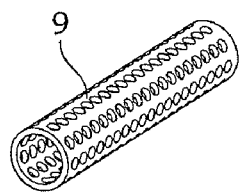
FIG. 8A-8D shows a process for the fabrication of a bio-artificial kidney according to another embodiment of the invention.
Figure 8B:
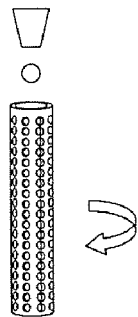
Figure 8C:
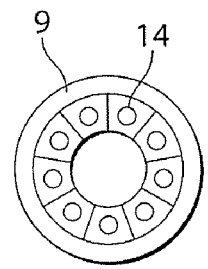
Figure 8D:
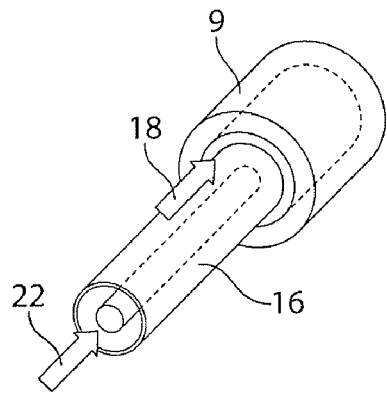

In some embodiments, a structure can be coated with a porous material (e.g., a polymer such as a gel), i.e., prior to being coated and/or printed with a surface-modifying substance. For instance, in the embodiment illustrated in FIG. 8, structure 9 can be fabricated using a three-dimensional fabrication method to form a bioartificial kidney. In some instances, the structure can be modified with a substance (FIG. 8B), i.e., the structure can be first coated with a porous polymer, and then with a surface-modifying substance such as collagen, i.e., to facilitate cell adhesion. Cells 14 can then be seeded into and/or onto the modified structure (FIG. 8C). FIG. 8D shows an assembled device comprising structure 9 seeded with cells (e.g., vascular cells). Structure 16 may include another layer of cells (e.g., proximal tubule cells). The device may mimic the function of a kidney, i.e., as blood flows according to arrow 18 and ultra-filtrate may flows according to arrow 22.

A porous polymer coating a structure can be used for a variety of purposes. For example, a porous polymer may be used to form small pores (i.e., having a cross sectional dimension on the order of 1-20 microns, or within the range of porosity of the polymer) within a larger pore (i.e., having a cross sectional dimension on the order of 20-200 microns) of the structure. In some cases, the porous polymer may allow sustained release of an active agent from the polymer, i.e., to facilitate cell growth and/or adhesion as a function of time. In other cases, the porous polymer can influence transport of components from a first to a second position of the structure. In yet other cases, a porous polymer coating a structure can reduce the surface roughness of the structure, as described below. One non-limiting example of a suitable porous polymer is polysulfone.

In some cases, structures can be fabricated to include substructures. For instance, a large vessel may be fabricated to include small vessels within the large vessel. Surfaces of substructures may also be modified, i.e., in a fashion described above. For example, in one embodiment, a wall of the large vessel may be modified with a first growth factor to induce growth of a first type of cell on the wall of the large vessel, and a wall of the small vessel may be modified with a second growth factor to induce growth of a second type of cell on the wall of the small vessel. Substructures may include pores that allow exchange of a component between an interior cavity portion of the substructure and a portion exterior to the substructure, i.e., between a cavity portion of the substructure and a cavity portion of a larger structure.

A wide variety of artificial tissues and organs can be fabricated as three-dimensional structures using methods described herein. In some embodiments, the structures can be used as templates for cell growth, which may be applied towards tissue engineering and/or organ replacement. For structures to be used in vivo, cells and/or tissues may be grown on a structure prior to the structure being implanted, or alternatively, the structure may be positioned directly into a mammalian system where the body's cells naturally infiltrate the structure.

In some particular embodiments, structures may be formed in the shape of organs that include a cavity portion. For instance, structures including a cavity portion may include hollow organs and/or epithelial organs such as vessels, lung, liver, kidney, pancreas, gut, bladder, and ureter, as described in more detail below. A cavity of a structure, as used herein, refers to a substantially enclosed space defined by a wall of the structure, in which a plane can be positioned to intersect at least one point within the cavity and the structure, where it intersects the plane, completely surrounds that point. The cavity and can be closed or open. For example, in one embodiment, a cavity may be defined by the interior space within a tube of a blood vessel. In another embodiment, a cavity may be defined by the hollow space inside a bladder. As such, cavities may have a variety of shapes and sizes. A space within a cavity is referred to as an interior cavity portion, and a space outside of the cavity is referred to as a portion exterior to the cavity. The cavity may be filled with fluid, air, or other components. In some cases, a cavity may be lined with one or more layers of cells or tissues. The layers of cells or tissues may form, for instance, membranes or walls of the tissue or organ. In some instances, the lining of a cavity can comprise pores that allow exchange of a component between a portion interior to the cavity and a portion exterior to the cavity, as described in more detail below.

A cavity of a structure may vary in volume and may depend, in some instances, on the tissue or organ in which the structure mimics. The volume of the cavity may be, for instance, less than 1 L, less than 500 mL, less than 100 mL, less than 10 mL, less than 1 mL, less than 100 microliters, less than 10 microliters, less than 1 microliter, less than 100 nanoliters, or less than 10 nanoliters, where volume is measured as within that portion of the structure that is enclosed.

A wall of structure defining a cavity portion can vary in thickness, and may also depend on the tissue or organ in which the structure mimics. In some cases, thick walls (i.e., greater than 500 microns thick) may be suitable for certain structures (e.g., bladder), i.e., requiring slow or relatively little exchange of components between portions interior and portions exterior to the cavity. Thin walls (i.e., less than 50 microns thick) may be applicable to some structures (e.g., alveoli), i.e., requiring quick exchange of components between portions interior and portions exterior to the cavity. In certain embodiments, a wall of a structure can be less than 1 mm thick, less than 500 microns thick, less than 200 microns thick, less than 100 microns thick, less than 50 microns thick, less than 30 microns thick, less than 10 microns thick, less than 5 microns thick, or less than 1 micron thick.

In some instances, a cavity may be defined by an inner diameter of a certain distance. "Inner diameter", as used herein, means the distance between any two opposed points of a surface, or surfaces, of a cavity. For example, the inner diameter of a blood vessel may be defined by the distance between two opposing points of the inner wall of the vessel. Inner diameters may also be used to describe non-spherical and non-tubular cavities. A cavity may have an inner diameter of, e.g., less than 10 cm, less than 1 cm, less than 1 mm, less than 500 microns, less than 200 microns, less than 100 microns, less than 50 microns, less than 30 microns, less than 10 microns, less than 5 microns, or less than 1 micron.

In some embodiments, a structure may include a cavity having more than one portion (i.e., in a case where the cavity portions are interconnected, thereby allowing a substance to pass freely between the cavity portions). Additionally or alternatively, the structure may include more than one cavities (i.e., in a case where the cavities are not interconnected). For instance, in one embodiment, a cavity of a structure may include at least a first and a second portion, the first portion of the cavity being defined by a first inner diameter and the second portion being defined by a second inner diameter. In another embodiment, a structure may include a first cavity having a first inner diameter and a second cavity having a second inner diameter. The second cavity may be defined, for instance, by that of a substructure. For the above cases, the first and second inner diameters may be different, i.e., the ratio of the first inner diameter to the second inner diameter can be greater than 1:1, greater than 2:1, greater than 5:1, greater than 10:1, greater than 20:1, greater than 50:1, greater than 100:1, greater than 200:1, or greater than 500:1. Some structures, such as certain vessels, may have a first cavity portion having the same inner diameter as that of a second cavity portion, i.e., the ratio of the inner diameters of the first and second portions may be 1:1. Additional examples of such structures are described in more detail below.

In mimicking tissues and/or organs of the body, different types of cells can be arranged proximate a structure in sophisticated micro-architectures that are responsible for the complex functions of the tissue or organ. Thus, microstructures having dimensions and arrangements closely related to the natural conditions of the tissue or organ can be formed. The design of the structure and the arrangement of cells within the structure can allow functional interplay between relevant cells, i.e., between cells cultured on the structure and those of the host environment. These factors may also enable appropriate host responses, e.g., lack of blood clotting, resistance to bacterial colonization, and normal healing, when implanted into a mammalian system.

The present inventors have realized the importance of addressing geometry, size, mechanical properties, and bioresponses in fabricating structures for tissue engineering and organ replacement, especially for structures involving hollow and epithelial organs, as described in more detail below.

In one aspect of the invention, tissues and organs of interest include those of the circulatory system. The circulatory system includes the heart (coronary circulation), the blood vessel system (systemic circulation), and the lungs (pulmonary circulation). The circulatory system functions to deliver oxygen, nutrient molecules, and hormones to the body, and to remove carbon dioxide, ammonia and other metabolic waste from parts of the body.

Coronary circulation refers to the movement of blood through the tissues of the heart. In some cases, portions of the heart become diseased, i.e., heart tissue may not receive a normal supply of food and oxygen, or certain structures forming the heart, e.g., heart valves, may not be operating normally. In the latter case, when heart valves are functioning properly, the flaps (also called leaflets or cusps) of the valves open and close fully. Proper function of heart valves may cease when the valves do not open enough or do not let enough blood flow through (i.e., stenosis), or when the valves do not close properly, allowing blood to leak into places where it shouldn't (i.e., incompetence or regurgitation). In these instances, heart valves may need to be replaced. In one embodiment, methods described herein can be used to fabricate heart valves (e.g., tricuspid, pulmonary, mitral, and/or aortic valves) that are coated with films of additives known to prevent blood clotting. In another embodiment, an artificial valve may incorporate additives such as antibiotics, which can prevent endocarditis, an infection of the heart's lining or valves. In some cases, an artificial valve may comprise a combination of additives, such as the ones mentioned above. The heart valves can be used in vivo to replace diseased heart valves, and/or in vitro as a scaffold template for cell seeding.

In another embodiment, three-dimensional fabrication techniques can be used to form structures of the blood vessel system, including arteries, veins, capillaries, and lymphatic vessels. The blood vessel system keeps blood moving around the body inside the circulatory system.

Arteries carry blood that is full of oxygen from the heart to all parts of the body. As the arteries get further away from the heart, they get smaller. Eventually arteries turn into capillaries, the smallest blood vessels, which go right into the tissues. Here, the blood in the capillaries gives oxygen to the cells and picks up the waste gas, carbon dioxide, from the cells. The capillaries are connected to the venules, the smallest veins in the body, and the veins get bigger as they carry the blood back towards the heart. The capillaries are the points of exchange between the blood and surrounding tissues. Components can cross in and out of the capillaries, i.e., by passing through or between the cells that line the capillary.

Figure 9A:
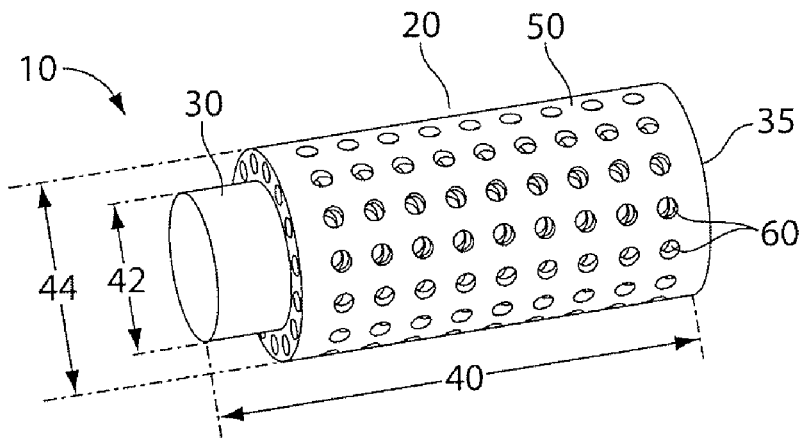
FIG. 9A is a schematic diagram showing a structure that can be used for the induction of vessels according to another embodiment of the invention.

Structures for use as templates for cell growth can be designed to mimic a variety structures of the blood vessel system. In some embodiments, structures can serve as templates for triggering controlled in-growth of vascular structures (FIG. 9) or complete artificial vessel replacements (FIG. 10). FIG. 9 shows structure 10, which can be used for the induction of vessels in vivo. Structure 10 was fabricated by a three-dimensional layering process, but other three-dimensional fabrication processes can also be used.

Figure 9B:
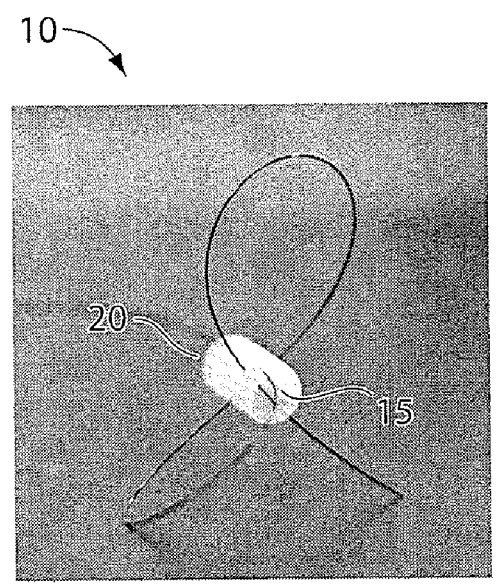
FIG. 9B is a photograph of a structure fabricated by a three-dimensional fabrication technique that can be used for the induction of vessels according to another embodiment of the invention.
Figure 10:
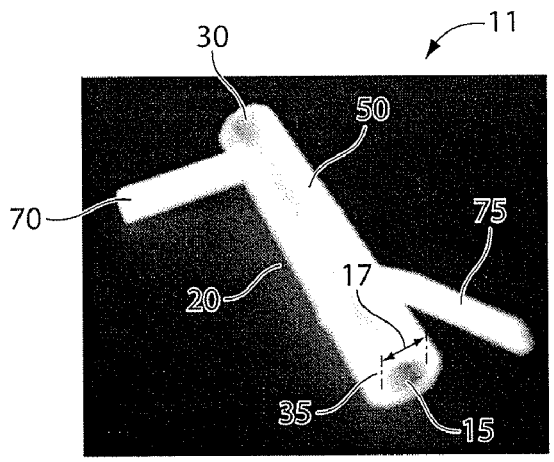
FIG. 10 is a photograph of a structure fabricated by a three-dimensional fabrication technique that can be used as a blood vessel according to another embodiment of the invention.

As illustrated in the embodiment shown in FIG. 9, structure 10 may be formed in the shape of a tube including interior cavity portion 15 (FIG. 9B) and a portion exterior to the cavity 20. Structure 10 may have a first end portion 30 and a second end portion 35, which may be opened or closed. In some cases, end portions 30 and 35 may be used to connect structure 10 to ducts of a patient. The dimensions of structure 10 may vary depending on the particular body part the structure will mimic, where the structure will be positioned in the body, the size of the patient, etc. For example, structure 10 may have an inner diameter 42 and/or outer diameter 44 of less than 10 mm, less than 5 mm (e.g., inner diameter of 0.5 mm and outer diameter of 1.5 mm), or less than 1 mm. In some embodiments, structure 10 to be transplanted into a mammalian body may have length 40 between 10 mm and 100 mm, or 25 mm and 75 mm (e.g., 50 mm), inner diameter 42 of 0.5 mm, and outer diameter 44 of 1.5 mm. The thickness of wall 50 of the structure may be defined by the difference between inner and outer diameters 42 and 44, respectively. Thicknesses of wall 50 can range from a few microns (i.e., a few cells) to millimeters thick.

In some cases, structure 10 can have a plurality of pores 60 in at least a portion of the structure. Pores 60 can vary in size; for instance, large pores (i.e., greater than 100 microns) may be suitable for growing large vessels through pores 60, and/or for facilitating high exchange of components between interior cavity portion 15 and portion 20 exterior to cavity. Small pores (i.e., less than 100 microns) may be suitable for growing small vessels through pores 60, and/or for facilitating relatively low exchange of components across wall 50. Structure 10 may be implanted into a mammal, or used in vitro.

In some cases, structures such as structure 10 may include one or more additional substructures. For instance, structure 10 may be fabricated to include a substructure such as a vessel. The substructure may be positioned in at least a portion within interior cavity portion 15, or it may be positioned exterior to cavity 15 (i.e., in portion 20 exterior to the cavity). In some cases, a substructure may pass across a pore (i.e., pore 60) of the structure, or the substructure may be interwoven between pores of the structure. As such, structure 10 may include at least a first cavity (i.e., interior cavity portion 15) and a second cavity (i.e., a cavity portion of the vessel). The ratio of the inner diameter of the first cavity to the inner diameter of the second cavity may be greater than 1:1, greater than 2:1, greater than 5:1, greater than 10:1, greater than 20:1, greater than 50:1, greater than 100:1, greater than 200:1, or greater than 500:1.

FIG. 10 shows structure 11, which can be used to replace a section of a blood vessel in a patient. Structure 11 includes interior cavity portion 15 having inner diameter 17, portion 20 exterior to the cavity, first end 30, and second end 35. As shown in the embodiment illustrated in FIG. 10, structure 11 also includes sections 70 and 75, which can be used as interconnecting lumens for connecting structure 11 to one or more ducts of a patient. If desired, a structure can be designed to include a plurality of such sections. Sections 70 and 75 may each be defined by cavity portions having a certain inner diameter. In some cases, the ratio of the inner diameter of a first cavity portion (e.g., interior cavity portion 15) to the inner diameter of a second cavity portion (e.g., cavity portion of section 70 or 75) can be equal to 1:1, greater than 1:1, greater than 2:1, greater than 5:1, greater than 10:1, greater than 20:1, greater than 50:1, or greater than 100:1.

Wall 50 of structure 11 may have a thickness of less than 5 mm, less than 1 mm (e.g., 0.5 mm), less than 0.5 mm. In one embodiment, wall 50 of structure 11 has a thickness of 0.5 mm. In some cases, wall 50 may be formed in an elastic material that allows stretching, recoiling, and absorption of pressure in response to pumping of the heart and fluid flow through the structure. Before implanting structure 11 into a patient, smooth muscle cells may be grown onto all, or portions, of wall 50. These muscle cells may contract and expand to control the diameter, and thus the rate of blood flow, through structure 11 (i.e., contraction and expansion of muscle cell may cause structure 11 to dilate and constrict, respectively). In some cases, an additional outer layer of connective tissue may be grown onto structure 11. A layer of elastic fibers may also be grown onto structure 11 to give it greater elasticity, if desired. In some embodiments, structure 11 can be made from a biodegradable polymer that degrades, i.e., after healthy tissues have re-grown and have integrated into the body.

In some embodiments, structures formed by methods described herein are designed to mimic capillaries, which can allow exchange of components such as nutrients, wastes, hormones, and white blood cells, between the blood and surrounding environment. The surrounding environment may include the interstitial fluid and/or surrounding tissues. The artificial structure may include a cavity portion comprising a wall having a thickness of 0.5 mm, for example, which can be lined with endothelial cells. In some cases, a wall of the capillary has a thickness of a single cell. In one embodiment, capillary structures may include small pores or holes that may be less than 50 microns, less than 10 microns (e.g., about 1 micron) in size between the cells of the capillary wall, allowing certain components to pass in and out of capillaries, i.e., between an interior cavity portion and a portion exterior to the cavity (e.g., the surrounding tissues). The pores may allow certain small components such as certain dissolved molecules (i.e., small ions) to pass across the pores, but may inhibit larger components such as proteins from passing across. In another embodiment, exchange of components across a capillary wall can occur by vesicles in the cells of the capillary wall that pick up components from the blood (i.e., in the interior cavity portion of the capillary), transport them across the capillary walls, and expel them into the surrounding tissue (i.e., into a portion exterior to the cavity of the capillary). In yet other embodiment, components may exchange between an interior cavity portion and a portion exterior to the cavity via passage through the cell lining. I.e., components may diffuse from the blood into the cells of the capillary walls, and then into the surrounding tissue. Artificial capillaries may also be designed to include one or more branching structures, which can create a greater surface area through which the exchange of components can occur.

In another aspect of the invention, structures are fabricated to mimic tissues and/or organs of the digestive track. The digestive tract encompasses the oral cavity, esophagus, stomach, small and large intestines, rectum, and anus. The different parts of the digestive tract may display a similar histo-architecture, i.e., each part may comprise a muscle wall that is covered by the mucosa, which contains epithelial cells. These organs can be affected by diseases such as cancer, infection, etc. Diseased organs of the digestive track typically require operations that include resections of the diseased segment. These removed segments can be replaced with artificial structures of the present invention. In some embodiments, structures can be fabricated to mimic a diseased section. The structure may be used as a scaffold for the in-growing of natural mucosa from healthy cells of a patient. This scaffold can then be implanted into the patient. In one embodiment, this approach is applied to so-called gut pouches to replace the continence function of the gut. Like artificial structures of the circulatory system, structures of the digestive track can be formed in biodegradable polymers.

Figure 11:
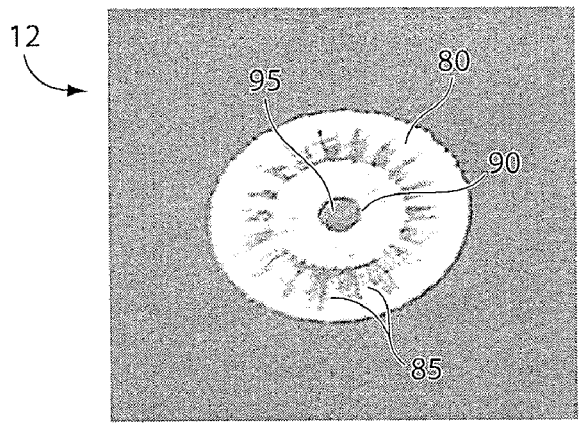
FIG. 11 is a photograph of an artificial liver lobule fabricated by a three-dimensional fabrication technique according to another embodiment of the invention.

In another aspect of the invention, structures are fabricated to mimic gut-associated glands. Gut-associated glands include the salivary glands, the liver, and the pancreas. All three organs are made up of specialized epithelial cells with endocrine and exocrine functions. In one embodiment, structures can be fabricated to mimic portions of the liver. The liver is comprised mainly of lobules containing hepatocytes that are arranged in plates. In between the hepatocyte plates, blood-containing sinusoids can be found. The center of the lobule is the central vein, and this vessel receives blood from the sinusoids. In some embodiments, artificial structures in the shape of liver lobules can be fabricated. FIG. 11 shows structure 12, an artificial liver lobule, which can be fabricated using a three-dimensional fabrication process. Structure 12 includes scaffold 80 for plating and growing hepatocytes. Scaffold 80 can be designed with a specific micro-architecture that allows spatial control of the seeding of cells. Structure 12 also includes sinusoidal structures 85, which can function as cavities for containing blood. The plates can be filled with hepatocytes in the inner space of scaffold 80, and plate wall 90 adjacent center 95 can be coated with endothelial cells. In certain embodiments, the liver lobules can have dimensions of approximately 0.7 mm×2 mm. Structure 12 can be fabricated to have pores that can facilitate exchange of a component. For example, exchange of a component may occur, i.e., via pores, between the blood contained in sinusoidal structures 85, i.e., an interior cavity portion, and the hepatocytes, which may be located at a portion exterior to the cavity. Pores can be fabricated to have a variety of sizes. Generally, for liver lobules, pores may be fabricated to have a cross-sectional dimension in the micron range.

In another embodiment, structures for tissue engineering and/or organ replacement can be fabricated to mimic portions of the pancreas. The pancreas is a mixed exocrine-endocrine gland that produces hormones such as insulin and glucagons, as well as pancreatic enzymes that help digest acids and macromolecular nutrients (e.g., proteins, fats and starch). The hormone-producing cells are aggregated in the islets of Langerhans. Pancreatic islets are scattered throughout the pancreas. Like all endocrine glands, pancreatic islets secrete their hormones into the bloodstream and not into tubes or ducts. Because of the need to secrete their hormones into the blood stream, pancreatic islets are surrounded by small blood vessels (i.e., capillaries). The islets are also highly vascularized, facilitating the exchange of hormones between the islets and the vessel system. In certain embodiments of the invention, structures in the shape of island-like structures are fabricated using techniques described herein. The artificial island-like structures can be designed to have a specific micro-architecture that can enable endocrine cells to be seeded in preformed locations, i.e., near structures that are designed to guide the capillaries. Like the structures described above, structures that mimic portions of the pancreas can be formed in biodegradable polymers if desired. These artificial pancreatic structures may be used to treat diseases such as diabetes mellitus.

In another aspect of the invention, structures are fabricated to mimic endocrine organs. The endocrine organs include the adrenals, thyroid, parathyroid, and pineal gland. These organs are made up of endocrine (i.e., hormone-producing) cells that are located very close to the capillaries, as described above for the islets of Langerhans. The close proximity of these organs to the capillaries allows the blood circulating factors to leave the capillaries and become bound to cell receptors on the endocrine cells, triggering the release of hormones. The released hormones diffuse into the capillaries, and are subsequently distributed in the body to bind with receptors in other tissues. In some embodiments, endocrine structures can be fabricated to have a specific micro-architecture that allows the seeding of cells within certain locations of the structure. Artificial endocrine organs may be fabricated to have a high degree of vascularization that facilitates the exchange of components between the organ and the capillaries. In some cases, artificial endocrine organs are made with high porosity. The pores may have a variety of sizes depending on the particular organ. Like the structures described above, structures that mimic endocrine organs can be formed in biodegradable polymers if desired. Artificial endocrine organs may be applied, for instance, towards treating insufficient production of hormones in glands.

In another aspect of the invention, structures are fabricated to mimic portions of the respiratory system. The respiratory system includes the trachea and the lungs. In one embodiment, a structure can be fabricated to replace diseased or damaged portions of the trachea. The trachea is a cartilaginous and membranous-ringed tube where air passes to the lungs from the nose and mouth. The trachea bifurcates into right and left mainstem bronchi. Artificial trachea may be fabricated to include similar architecture and mechanical properties to that of healthy trachea. For instance, the artificial structure may include ring-like portions made from an elastic polymer that resembles cartilage. In some cases, cartilage cells (e.g., hyaline cartilage) from healthy trachea can be seeded and grown into the artificial structure. The artificial structures can be lined with ciliated cells, used to remove foreign matter (e.g., dust) from the airway so that they stay out of the lungs.

In one embodiment, a structure can be fabricated to replace diseased or damaged portions of the lung. The lungs include air-conducting segments such as the bronchioles, numerous small tubes that branch from each bronchus (a branch of the trachea) into the lungs. The lungs also include the alveoli, the respiratory portions where gas exchange takes place. The air-conducting portions include a wall that is lined by respiratory epithelium, which is responsible for producing mucous fluid. In some cases, structures are fabricated to mimic portions of the air-conducting segments. For instance, artificial bronchioles may be fabricated to have a thickness of less than 10 mm, less than 1.0 mm (e.g., 0.5 mm), or less than 0.5 mm, and a diameter of less than about 10 mm, less than about 5 mm (e.g., 2 mm), or less than about 2 mm. The thickness and diameter of the bronchiolar structure will depend, of course, on the position of the structure within the lung, the size of the patient, etc. All structures of the air-conducting portion can be formed as the artificial interposed segments or as templates for engineered tissue constructs. For instance, in some cases, the artificial structure may form a scaffold for growing connective tissue and smooth muscle cells within the walls of the structure. The walls may also be lined with epithelial cells, which can comprise three types of cells: ciliated cells, non-ciliated cells, and basal cells. In some particular embodiments, certain artificial structures, such as those that mimic terminal bronchioles, can be fabricated to include artificial alveoli in the walls of the structure.

In some embodiments, structures are fabricated to mimic alveoli. Alveoli are small, thin-walled air sacs (i.e., cavities) at the end of the bronchiole branches having cross-sectional dimensions on the order of 200 microns. Proximate the alveolar walls are pulmonary capillaries where gas exchange occurs between blood in the capillaries and inhaled air in the alveoli. For instance, to reach the blood, oxygen diffuses through the alveolar epithelium, a thin interstitial space, and the capillary endothelium; carbon dioxide follows the reverse course to reach the alveoli. In certain embodiments of the invention, artificial alveolar structures can be fabricated with natural dimensions and with porous walls for gas exchange. Pores in the walls of the alveoli may allow exchange of a component (e.g., a gas) between an interior portion of the alveoli (i.e., an interior cavity portion) and the interstitial space surrounding the alveoli (i.e., a portion exterior to the cavity portion). Artificial alveolar structures may be formed in an elastic material that gives the alveoli mechanical stability while allowing expansion and contraction of the structures. In some cases, the artificial alveolar structures may form scaffolds for growing cells, i.e., the structures may be lined with epithelial cells such as Type 1 and Type 2 pneumocytes. Artificial alveoli can be used to help increase the oxygen content in patients with respiratory deficiencies.

Figure 12:
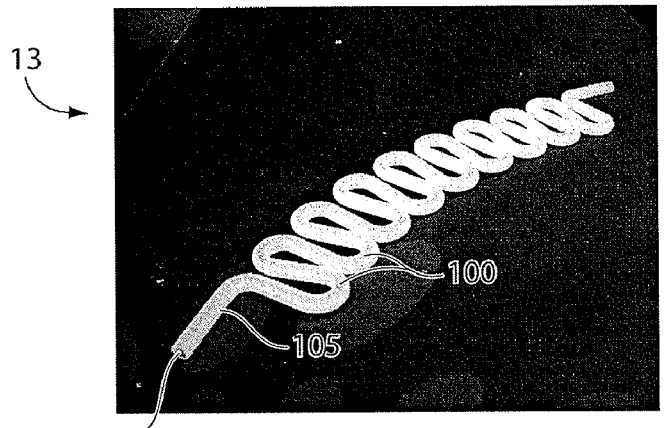
FIG. 12 is a photograph of a structure fabricated by a three-dimensional fabrication technique that can be used to mimic the function of certain portions of the urinary system according to another embodiment of the invention.

In another aspect of the invention, structures are fabricated to mimic portions of urinary system. The urinary system comprises the kidneys, ureters, the urinary bladder, and the urethra. In some cases, a structure can be fabricated to replace diseased or damaged portions of the kidney. The kidney is formed from a plurality of nephrons, which include the glomerulus and the proximal and distal convoluted tubules. The glomerulus represent the filtration stations, which contain tuffs of capillaries where the ultrafiltrate is pressed out. In some embodiments, a structure can be fabricated in the form of a porous looped superstructure, such as structure 13 shown in FIG. 12. In one embodiment, structure 13 can be used as an artificial glomerulus. In another embodiment, structure 13 can be used as artificial proximal and/or distal convoluted tubules. As shown in the embodiment illustrated in FIG. 12, structure 13 can include a plurality of loops 100, which can be of the same or different dimensions. Structure 13 can include at least one wall 105 defining cavity 110 (i.e., a tubular portion). Cavity 110 can have the same inner diameter throughout the structure, i.e., of about 40-500 microns, 50-100 microns. Alternatively, a first portion of the cavity may have an inner diameter different than that of a second portion of the cavity. The thickness of wall 105 can range from about 1-500 microns (e.g., 2-500 microns), 1-100 microns, or 2-100 microns. Wall 105 may optionally include a plurality of pores that enable exchange of a component (e.g., water and ions) between a portion interior to the cavity and a portion exterior to the cavity. The pores may allow certain components to pass between interior and exterior portions of the cavity, e.g., based on size, charge, etc. In some cases, all, or portions, of wall 105 can be covered with films of nanometer to micron thickness. These films can form selective permeable membranes allowing certain components to pass between interior and exterior portions of the cavity. Structure 13 may be used to process ultrafiltrate in such a way that the good substances (e.g., glucose and amino acids) become reabsorbed, and the wastes (e.g., urea) get discarded as urine. In certain embodiments, structure 13 can act as a hemofiltration system. Accordingly, structures such as structure 13 can be used to replace and/or aid the filtration function of the kidney.

Figure 13A:
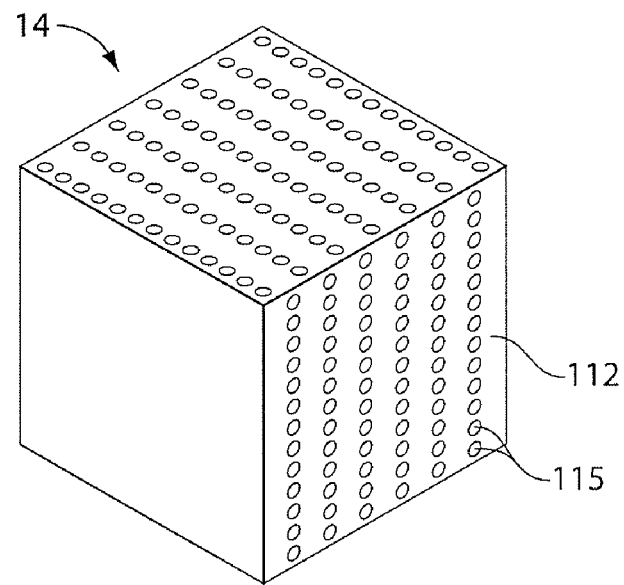
FIGS. 13A and 13B show a block comprising a plurality of cavities according to another embodiment of the invention.
Figure 13B:
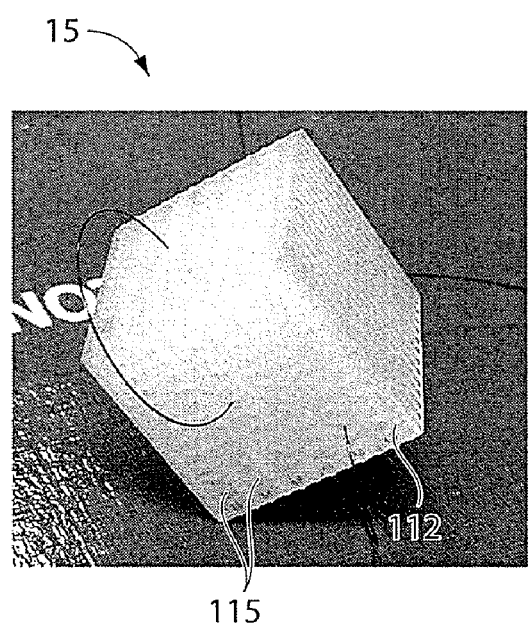

Some embodiments of the invention include the formation of a plurality of cavities within a structure. For example, in the embodiment illustrated in FIG. 13, structures 14 and 15 are formed in the shape of a block, and include wall 112 that defines a plurality of cavities 115. Cavities within the structure may be separate, i.e., as shown in FIG. 13A, or they may be interconnected, i.e., as shown in FIG. 13B. Cavities within the structure may have the same or different geometry and/or dimensions. Structures having a plurality of cavities can be used, for instance, to improve the surface-to-volume ratio in a hemofiltration system, i.e., for higher rate of reabsorption of electrolytes such as glucose and other metabolic products. In some cases, structures 14 and/or 15 may be combined with other embodiments of the invention. For instance, structures 14 and/or 15 can be combined with one or more artificial glomeruli to replace the main renal function with an extracorporeal module. In other instances, structures 14 and/or 15 can be combined with one or more artificial glomeruli as an implantable device to replace the main renal function in a mammalian system.

In some cases, structures such as structures 14 and/or 15 may include one or more additional substructures. For instance, structure 14 and may be fabricated to include a substructure such as a vessel. The substructure may be positioned in at least a portion of cavity 115, or it may be positioned exterior to cavity 115. In some cases, a substructure may be interwoven between more than one cavities of the structure. As such, structure 14 may include at least a first cavity (i.e., a cavity 115) and a second cavity (i.e., a cavity portion of the vessel), the ratio of the inner diameter of the first cavity to the inner diameter of the second cavity being greater than 1:1, greater than 2:1, greater than 5:1, greater than 10:1, greater than 20:1, greater than 50:1, greater than 100:1, greater than 200:1, or greater than 500:1.

In some cases, an artificial structure can be fabricated to replace diseased or damaged portions of the ureter and/or bladder. The ureter and bladder are hollow organs that include a wall, lined by a transitional epithelium, defining a cavity portion. Sometimes, this epithelium can be affected by cancer. Typically, to treat such a disease, a surgical operation is necessary whereby portions of the gut are removed and used to replace the reservoir function of the bladder, or the conductive function of the ureters. In some cases, this procedure causes the urethra to be affected by infection, leading to urethra stenosis. To circumvent these complications, diseased portions of the ureter and/or bladder may be replaced using artificial structures of the invention. Artificial structures may also be used to replace portions of the ureter and/or bladder to treat conditions such as urinary incontinence.

Figure 14:
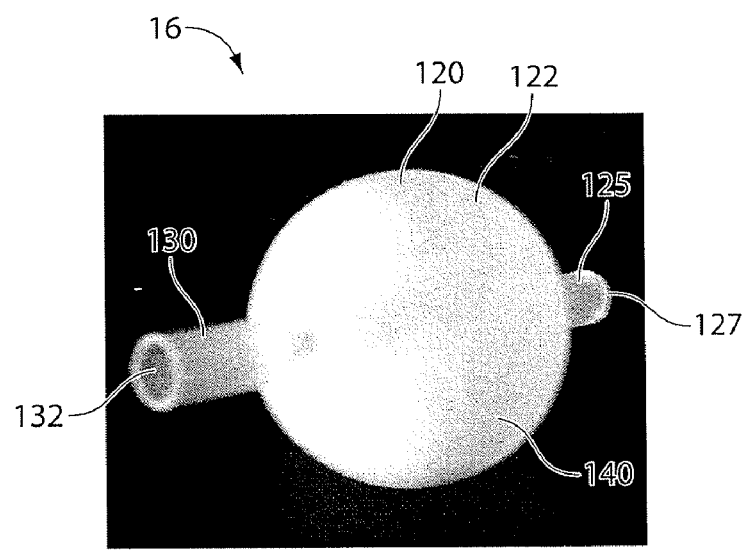
FIG. 14 is a photograph of an structure fabricated by a three-dimensional fabrication technique that can be used to mimic the function of a bladder according to another embodiment of the invention.

Structures formed by three-dimensional fabrication techniques can be used to replace portions of the ureters or urethra, or, they may be employed as artificial urinary bladders. The structures may be used for tissue engineering and/or organ replacement, in vivo or ex vivo. FIG. 14 shows structure 16, an artificial bladder, including main body portion 120, inlet 125 for connecting to the ureters, and outlet 130 for connecting to the urethra. Structure 16 includes wall 140 defining cavity portion 122 of the main body portion (i.e., a first cavity portion), cavity portion 127 of the inlet (i.e., a second cavity portion), and cavity portion 132 of the outlet (i.e., a third cavity portion). Cavity portions 122, 127, and 132 may have inner diameters ranging from about 0.01-5 mm, or 0.01-2 mm. In some instances, one cavity portion may have an inner diameter that is different from the inner diameter of another cavity portion of the structure. For example, the ratio between inner diameters of second cavity portion 127 and first cavity portion 122 may be greater than 1:1, greater than 2:1, greater than 5:1, greater than 10:1, greater than 20:1, greater than 50:1, or greater than 100:1.

Wall 140 may have a thickness ranging from 0.01-5 mm, or 0.01-2 mm, depending on the volume of liquid in the artificial bladder, and may be formed in a flexible material to allow expansion and contraction of the bladder. In some cases, wall 140 is lined with cells and/or tissues before implanting the structure into a patient. For instance, structure 16 may serve as a template for different layers of tissues that form the bladder, i.e., the mucosa, submucosa, and muscularis layers. The mucosa includes the transitional epithelium layer, which can serve as a selective barrier between the organ an environment exterior to the organ. Underneath the epithelium layer can include the basement membrane, a single layer of cells separating the epithelial layer from the submucous layer (lamina propria). The submucous layer includes connective tissue that is interlaced with the muscular coat. The submucous layer can contain blood vessels, nerves, and in some regions, glands; in some embodiments, structure 16 can include such micro-architectures. Muscle cells defining the muscular layer may be positioned underneath the submucous layer.

A variety of materials can be used to fabricate structures of the present invention. Materials used to form structures for tissue engineering and/or organ replacement may be biocompatible, and can include synthetic or natural polymers, inorganic materials, or composites of inorganic materials with polymers. In the description herein concerning the use of appropriate materials to fabricate structures, those of ordinary skill in the art can select materials, techniques, etc. based upon general knowledge of the art and available reference materials concerning certain techniques for fabrication, in combination with the description herein.

In some embodiments, structures are formed in photocurable polymers. For instance, photocurable polymers may include ultra-violet or visible-light curable polymers. Particular materials include acrylic systems, and polyethylene oxide precursors terminated with photo-crosslinking end groups. In some cases, acrylate-based photo-polymers can include components such as a sensitizer dye, an amine photo-initiator, and a multifunctional acrylate monomer. For example, pentaerythritol triacrylate (PETIA,) can form the backbone of the polymer network, N-methyldiethanolamine (MDEA) can be used as a photo-initiator, and Eosin Y (2-, 4-, 5-, 7-tetrabromofluorescein disodium salt) can be used as a sensitizer dye. This system is particularly sensitive in the spectral region from 450 to 550 nm, and can be used, for instance, in two-photon lithography involving a 1028 nm laser. In another example, an organic-inorganic hybrid such as ORMOCER® (Micro Resist Technology) can be used to fabricate artificial structures for tissue engineering and/or organ replacement. This material can show high transparency in the visible and near infrared ranges, can contain a highly crosslinkable organic network, can incorporate inorganic components that may lead to high optical quality and high mechanical and thermal stability, and can be biocompatible for certain types of cells and/or cellular components. In yet another example, acrylate and epoxy polymers such as ethoxylated trimethylolpropane triacrylate ester and alkoxylated trifunctional acrylate ester can be used to form structures.

In certain embodiments, photopolymerizable materials that are also biocompatible and water-soluble can be used to form structures for tissue engineering and/or organ replacement. A non-limiting example includes polyethylene glycol tetraacrylate, which can be photopolymerized with an argon laser under biologically compatible conditions, i.e., using an initiator such as triethanolamine, N-vinylpyrrolidone, and eosin Y. Similar photopolymerizable units having a poly(ethylene glycol) central block, extended with hydrolyzable oligomers such as oligo(d,l-lactic acid) or oligo(glycolic acid), and terminated with acrylate groups, may be used.

A structure may be formed in a material that is non-biodegradable or biodegradable (i.e., via hydrolysis or enzymatic cleavage). In some embodiments, biodegradable polyesters such as polylactide, polyglycolide, and other alpha-hydroxy acids can be used to form structures. By varying the monomer ratios, for example, in lactide/glycolide copolymers, physical properties and degradation times of the polymer can be varied. For instance, poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded.

In some cases, structures formed in biocompatible polymers having low melting temperatures are desired. Non-limiting examples include polyethylene glycol (PEG) 400 (melting temperature=4-80° C.), PEG 600 (melting temperature=20-25° C.), PEG 1500 (melting temperature=44-480° C.), and stearic acid (melting temperature=70° C.).

Other polymers that can be used to form structures include ethylene vinyl acetate, poly(anhydrides), polyorthoesters, polyphosphazenes, and protein polymers such as albumin, collagen, and polysaccharides. Examples of such polymers include, but are not limited to, FullCure 720 from Objet® and RenShape SL Y-C9500 from Huntsman®.

In some embodiments, non-polymeric materials can be used to form structures for tissue engineering and/or organ replacement. Non-limiting examples of such materials include organic and inorganic materials such as ceramics, glass, hydroxyapatite, calcium carbonate, buffering agents, as well as drug delivery carriers (e.g., gels), which can be solidified by application of an adhesive or binder.

In certain embodiments, additives can be added to a structure. Additives may, for instance, increase a physical (e.g., strength) and/or chemical (e.g., hydrophilicity) property of the material in which the structure is formed. Additives can be dispersed throughout the material of a structure, and/or can be incorporated within certain region(s) of a structure. In some cases, additives can be incorporated during formation of the structure by a three-dimensional fabrication process; in other cases, additives can be incorporated into the structure after the overall shape of the structure has been formed. Additives can also be incorporated into and/or onto a structure by adsorption or by chemically reacting the additive onto the surface of the polymer, i.e., by coating or printing the additive onto the structure. Non-limiting examples of additives include bioactive agents (e.g., therapeutic agents, proteins and peptides, nucleic acids, polysaccharides, nucleic acids, and lipids, including anti-inflammatory compounds, antimicrobial compounds, anti-cancer compounds, antivirals, hormones, antioxidants, channel blockers, and vaccines), surfactants, imaging agents, and particles. If desired, additives may be processed into particles using spray drying, atomization, grinding, or other standard techniques. In some cases, additives can be formed into emulsifications, micro- or nano-particles, liposomes, or other particles that can be incorporated into the material of a structure. In some embodiments, composite structures for tissue engineering and/or organ replacement can be formed by combining inorganic and organic components. Particles incorporating an additive can have various sizes; for example, particles may have a cross-sectional dimension of less than 1 mm, less than 100 microns, less than 50 microns, less than 30 microns, less than 10 microns, less than 5 microns, less than 1 micron, less than 100 nanometers, or less than 10 nanometers.

In some cases, it is desirable to release an additive from portions of a structure when the structure is in its environment of use (e.g., implanted in a mammalian body). Release of an additive may include hydrolysis and/or degradation of the polymer forming the structure. The release rate of the additive can be determined, in some instances, by the degradation rate of the polymer. The release rate of the additive can be controlled by the distribution of the additive throughout the polymer and/or by variation of the polymer microstructure (e.g., density of the polymer) such that the degradation rate varies with certain portions of the structure.

Figure 15A:
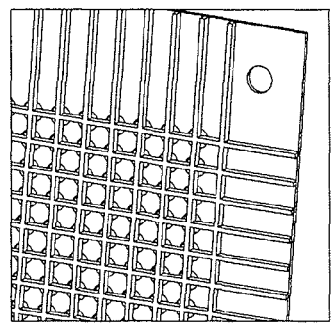
FIGS. 15A and 15B show schematic diagrams of a backside and frontside surface design of overlapping holes according to another embodiment of invention.
Figure 15B:
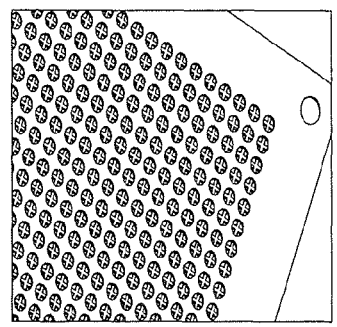
Figure 15C:
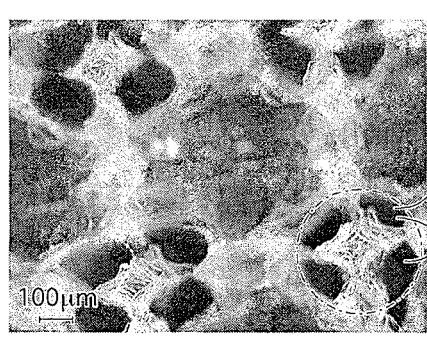
FIG. 15C shows a microscope image of holes fabricated in a polymer according to the design of FIGS. 15A and 15B according to another embodiment of invention.
Figure 15D:
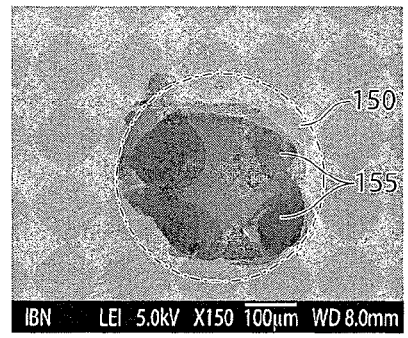
FIG. 15D shows an SEM micrograph of holes created by overlapping larger holes according to another embodiment of invention.
Figure 15E:
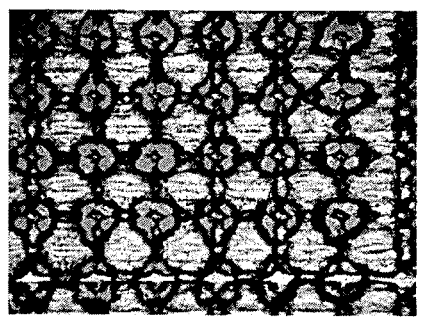
FIGS. 15E and 15F show microscope and SEM images, respectively, of holes created by overlapping larger holes according to another embodiment of invention.
Figure 15F:
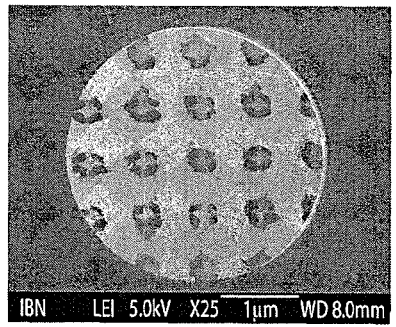

A variety of methods can be used to create porous structures that can vary in size and shape in three-dimensions. For instance, pores can be fabricated directly by a three-dimensional fabrication technique used to fabricate the structure. In some cases, to reduce the pore size and/or to form overlapping pores in a structure, pores can be designed and printed with an offset. For instance, FIG. 15A shows a front-side design of overlapping pores; FIG. 15B shows the back-side of the design. FIGS. 15C-15F show overlapping pores fabricating by three-dimensional printing. As illustrated in FIGS. 15C and 15D, first pore 150 having a first cross-sectional dimension can at least partially overlap with second pores 155 having a second cross-sectional dimension. Using this method, multiple pores can be fabricated within a larger pore. This method can allow the reduction of effective pore size; for example, as shown in FIG. 15C, pore 150 having a cross-sectional dimension of 200 μm can be used to form pores 155 having a cross-sectional dimension of 80 μm.

Figure 15G:
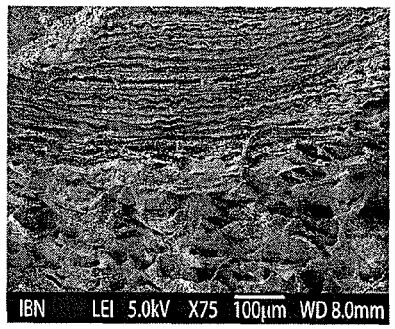
FIG. 15G shows a cross-section of a porous polymer coating a tubular structure according to another embodiment of invention.
Figure 15H:
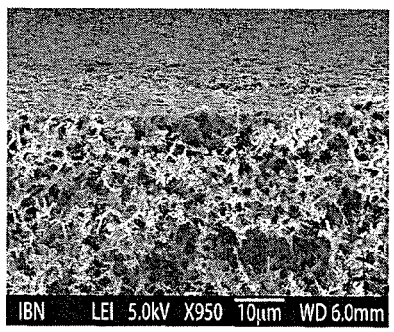
FIG. 15H shows a micrograph of the porous polymer shown in FIG. 15G according to another embodiment of invention.

To further reduce the pore size of a structure, a porous material can be used to coat a surface of the structure. In some cases, a porous material may include more than one component having different solubility in certain solvents. For example, a first component may include the polymer in which the structure is formed, and a second component may include particles that are not soluble in the polymer, but which can be subsequently dissolved in a solvent that dissolves the particles. After the structure is coated with the porous material, the structure can be soaked in a solvent that dissolves the second component, i.e., to leach out the second component from the porous material. As shown in FIGS. 15G and 15H, this process can form highly porous materials that can adhere well to structures formed by three-dimensional printing.

In one embodiment, pores can be formed in a structure by printing a polymer solution onto a bed of particles (e.g., salt, sugar, and polyethylene oxide) that are not soluble in the polymer, but which can be subsequently dissolved in a solvent that dissolves the particles, but not the polymer. In this case, the polymer that forms the structure can be printed onto a bed of the particles; the device can then be removed from the powder bed and placed in an appropriate solvent. For example, a structure formed in polylactic acid can be formed by printing a polylactic acid solution onto a bed of glucose particles, and the glucose can subsequently be leached with water. In some instances, a polymer solution can be printed onto a bed of particles that are partially soluble in the printed solvent. For instance, a polylactic acid solution can be printed onto a bed of polyethylene oxide particles, which can allow the polyethylene oxide to penetrate into the surface of the polylactic acid. After printing, the polyethylene oxide can be dissolved and leached out of the polymer with water.

In another embodiment, pores can be formed in a structure by printing a polymer solution onto a heated bed of polymer. In yet another embodiment, pores can be formed by printing a polymer solution onto a bed containing a foaming agent.

In some cases, porosity may be induced in the structure after the overall shape of the three-dimensional structure has been formed. For instance, in one embodiment, a porous polymer can be associated with pores of the structure to form smaller pores within larger pores of the structure, as described above. In another embodiment, pores can by formed in a structure after the structure has been placed in an environment that causes degradation or resorption of portions of the structure. I.e., a structure formed in a polymer can be implanted into a mammal, and pores within the polymer can be formed by bioresorption of the polymer. In some embodiments, existing pores or features within the structure can be modified (e.g., expanded, interconnected, etc.) by these or similar techniques.

Figure 16A:
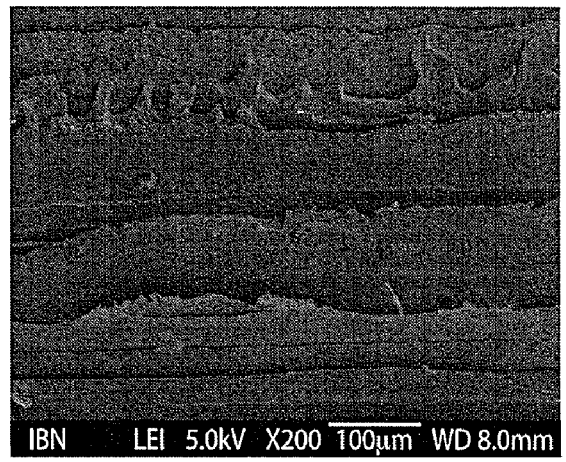
FIG. 16A shows an SEM micrograph of the surface of a horizontally-printed structure using an Eden 260 RPT according to another embodiment of invention.
Figure 16B:
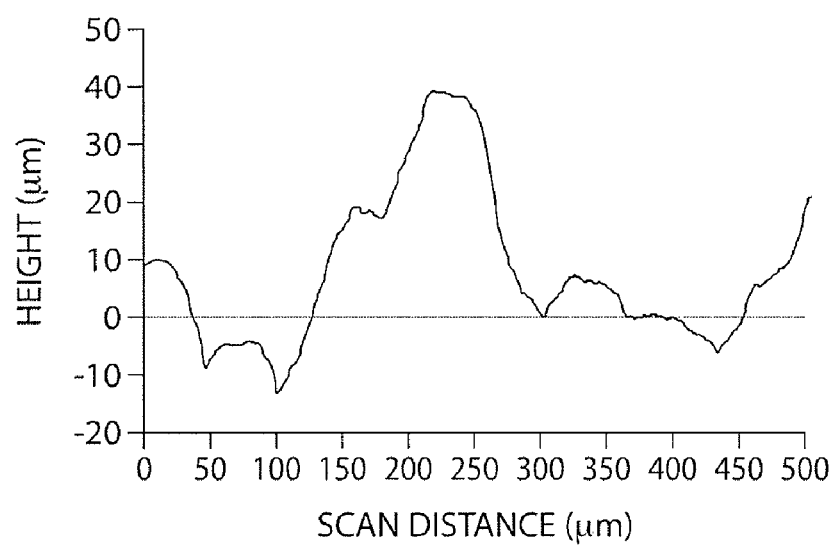
FIG. 16B shows a profiler scan of the surface shown in FIG. 16A according to another embodiment of invention.
Figure 17A:
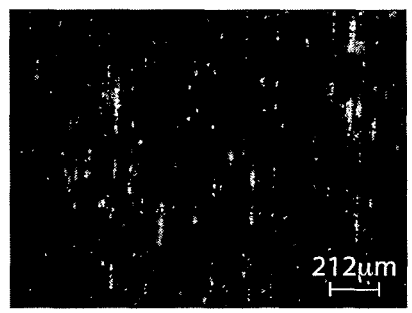
FIGS. 17A to 17D show microscope images of cells seeded on the surface shown in FIG. 16A according to another embodiment of invention.
Figure 17B:
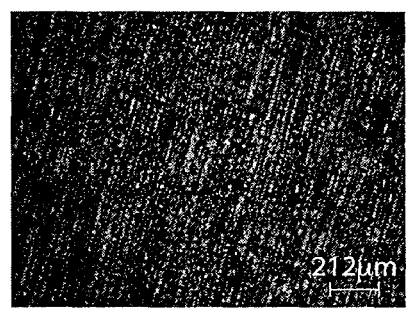
Figure 17C:
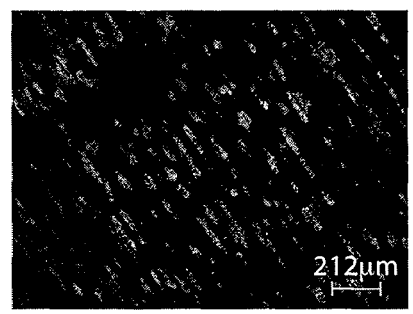
Figure 17D:
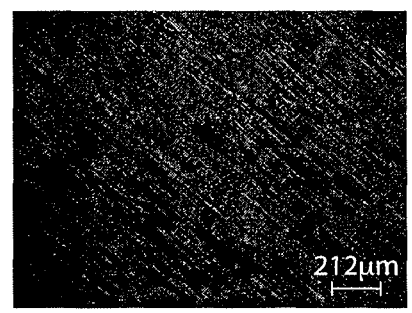

Sometimes, a structure may have surface roughness when it is fabricated using a three-dimensional printing technique. For instance, in the embodiment illustrated in FIG. 16A, surfaces of some structures fabricated using the Eden 260 RPT had a roughness of 3 microns and a waviness of 40 microns peak to peak, FIG. 16B. In some cases, cells seeded directly on these surfaces aligned themselves along the grooves of the printed surfaces. For instance, for surfaces that were coated with fibronectin, endothelial cells (HMEC-1) and tubule cells (MDCK) aligned to the grooves of the surfaces, as shown in FIGS. 17B and 17D, respectively. FIGS. 17A and 17C show endothelial and tubule cells, respectively, on surfaces that were not coated with fibronectin.

Surface roughness may be reduced using a variety of methods. Non-limiting examples of methods that can reduce surface roughness include coating surfaces with a material (e.g., synthetic materials such as cyanoacrylate and polysulfone/polymethylmethacrylate (PMMA), or biomaterials), and manipulating the print direction of the surface.

Figure 18A:
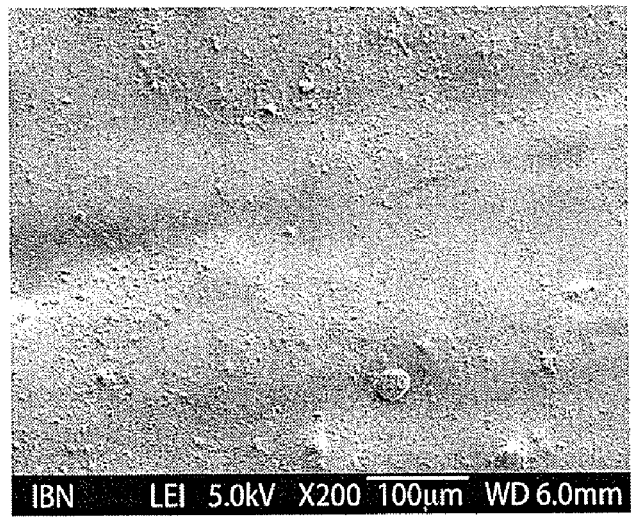
FIG. 18A shows an SEM micrograph of cyanoacrylate-coated structure according to another embodiment of invention.
Figure 18B:
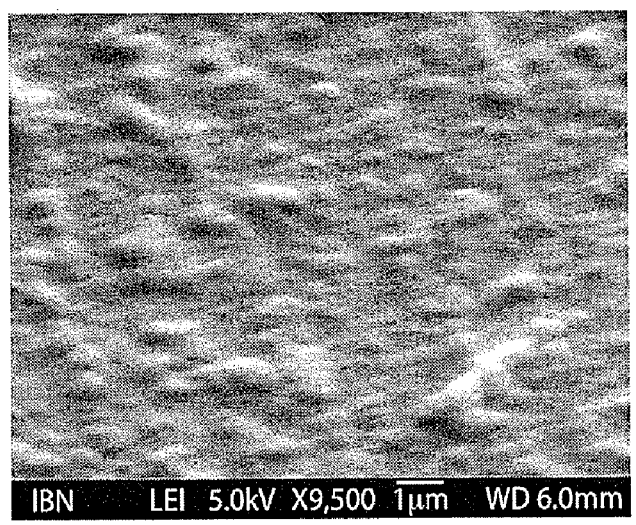
FIG. 18B shows a high magnification image of the surface shown in FIG. 18A according to another embodiment of invention.
Figure 19:
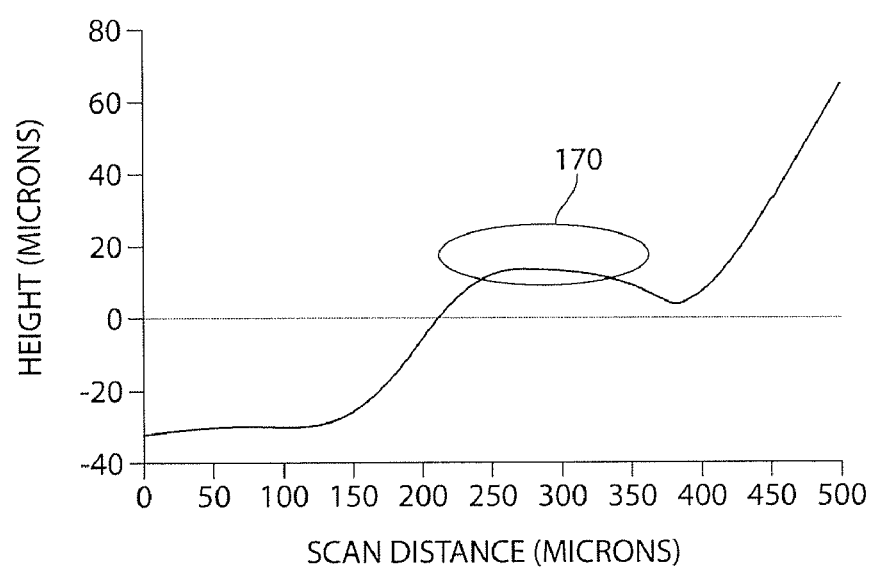
FIG. 19 shows a profilometer scan of the internal surface of a tubular structure according to another embodiment of invention.

FIG. 18A shows an SEM image of a surface of a structure (i.e., the internal surface of a tube having a diameter of 2 mm) fabricated by three-dimensional printing after modification of the surface with a coating of cyanoacrylate to reduce surface roughness. FIG. 18B is a high resolution SEM image of FIG. 18A. FIG. 19 shows a profilometer scan of the internal surface of the structure after modification using cyanoacrylate. Inconsistencies in measurements within area 170 of FIG. 19 are believe to be artifacts of the probe tip used in measuring roughness. From both the SEM micrograph and the profilometer scan, it was observed that surface roughness as well as the waviness of printed structure was significantly reduced by coating the surface.

Figure 20A:
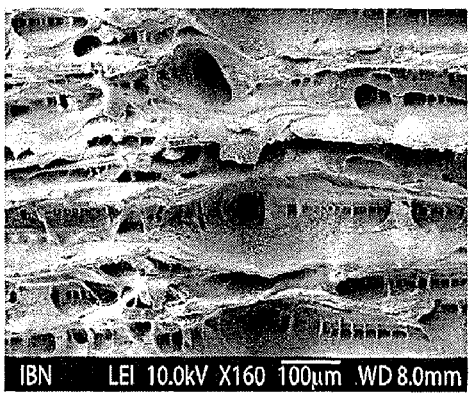
FIG. 20A shows an SEM micrograph of a surface of a horizontally printed structure according to another embodiment of invention.
Figure 20B:
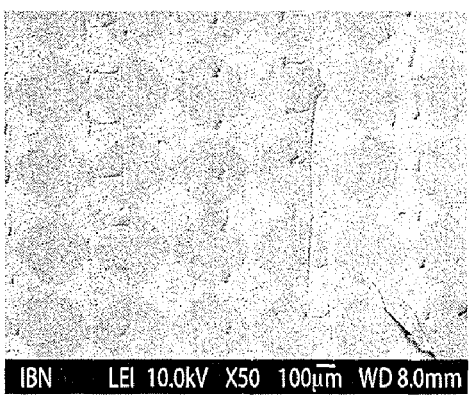
FIG. 20B shows an SEM micrograph of a surface of a vertically printed structure according to another embodiment of invention.
Figure 21:
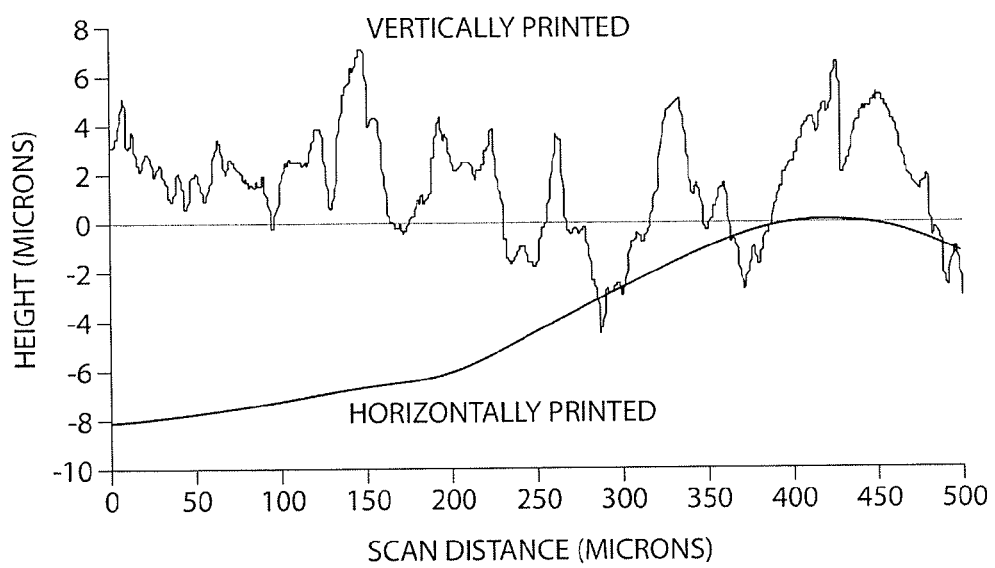
FIG. 21 shows a profilometer scan of vertically and horizontally printed structures according to another embodiment of invention.

Initial surface roughness and waviness of a surface of a structure formed by three-dimensional printing can be reduced by controlling the print direction of the desired surface. To determine the effects of print direction of surface on surface roughness, a structure was printed horizontally and vertically. FIGS. 20A and 20B show SEM images of surfaces of structures that were printed horizontally and vertically, respectively. FIG. 21 shows a profilometer scan of both surfaces shown in FIGS. 20A and 20B. In these embodiments, the vertically printed membrane had high surface roughness but was fairly flat with very little waviness observed. On the other hand, the horizontally printed membrane had a fairly smooth surface but was wavy. In some instances, structures formed by vertical printing may be more appropriate for cell culture.

Figure 20C:
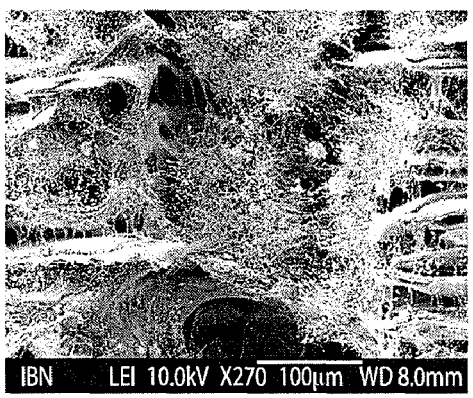
FIGS. 20C to 20F show surfaces of structures coated with various materials according to another embodiment of invention.
Figure 20D:
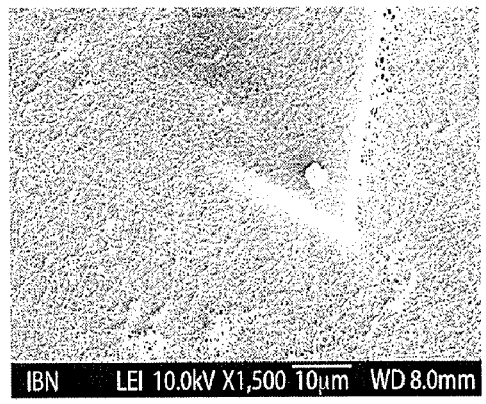
Figure 20E:
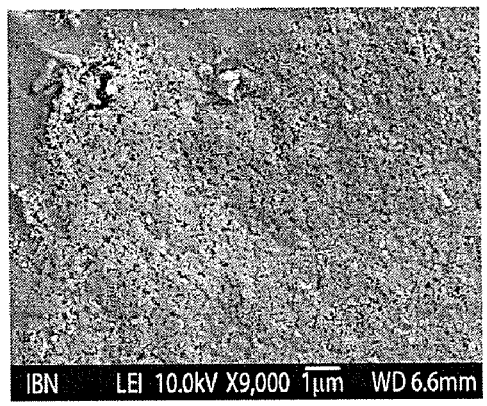
Figure 20F:
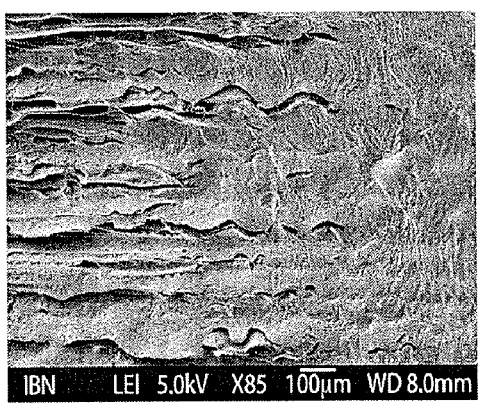

Vertically and horizontally printed structures can be coated with other materials such as collagen type 1, fibronectin, and porous materials such as polysulphone. FIG. 20C shows a surface that had been modified with collagen. FIG. 20D shows a horizontally printed half-pipe covered with collagen with reduced surface roughness. FIGS. 20E and 20F show a polysulphone coated half-pipe at high and low magnification, respectively. At high magnification, (FIG. 20E) it can be observed that the polysulphone coating on the surface of a printed superstructure provides a uniform density of pores on the thin film, enhancing fluid transport from the cell through the porous thin film to the macro pores on the printed structures into the outer compartment. FIG. 20F shows, at lower magnification, that surface roughness (in the range of 100 microns) of the printed structures is reduced (i.e., smoothed). From SEM micrographs, it was observed that surface roughness of 3-4 microns can be reduced with a coating of collagen or fibronectin. A porous material can also reduce surface roughness and/or waviness of a surface. For instance, polysulphone was spun at 2500 RPM onto the surface of a tube with internal diameter of 2 mm, and the material was allowed to polymerize and coat the inner surface of tube. This porous material was able to provide a similar smoothness to that achieved using cyanoacrylate.

The following examples are intended to illustrate certain embodiments of the present invention, but are not to be construed as limiting and do not exemplify the full scope of the invention.

EXAMPLE 1

Characterization of Pore Sizes Fabricated by Three-Dimensional Printing

For the formation of structures that can allow the transport of components, such as soluble factors between portions of the structure, pores can be designed and printed on the structures. To characterize the minimum pore size obtainable with the Eden 260 RPT, a 500 µm thick stencil was designed with pores sizes ranging from 100 µm to 1000 µm, in intervals of 100 µm, and printed (FIG. 3). After the stencil had been printed, the bulk of the support material was peeled. Next, the stencil was rinse with de-ionized water and immersed in 25% tetra methyl ammonium hydroxide (TMAH) solution and the pore sizes were measured over time (FIG. 4). Complete removal of sacrificial material on the super structure was typically achieved within 5 hours of TMAH immersion.

EXAMPLE 2

Characterization of Surface Roughness of Structures Fabricated by Three-Dimensional Printing Roughness of surfaces of structures fabricated using the EDEN 260 RPT were measured with an AlphaStep profiler. The surfaces had a RMS roughness of 3 microns and waviness of 40 microns (peak to peak), as shown in FIG. 16. Typical sizes of cells seeded onto surfaces of printed structures ranged from 10-30 µm in diameter.

To examine the influence of surface roughness on cell culture, endothelial and tubule epithelial cells were seeded onto printed semi-tubular structures. Madin-Darby Canine Kidney cells (MDCK) were obtained from American Type Culture Collection (Rockville, USA). The endothelial cell type (HMEC-1) was provided by the National Center for Infectious Diseases (Atlanta, USA). All cell types were cultured in DMEM (Invitrogen Singapore, Singapore) with 10% fetal calf serum (Invitrogen Singapore, Singapore) and 1% antibiotic-antimycotic solution (Invitrogen Singapore, Singapore). Cells seeded on to the structures were suspended in the culture medium and allowed to grow. To observe cell adhesion on printed surfaces, cells were fixed in ice-cold ethanol for 10 minutes. After several rinses with phosphate-buffered saline (PBS), the samples were incubated with blocking solution containing PBS, 10% fetal calf serum (FCS), and 1% bovine serum albumin (BSA) for 30 minutes. The primary antibodies were incubated for 1.5 hours in blocking solution. The antibody (Santa Cruz Biotechnologies, Santa Cruz, USA) was diluted at a ratio of 1:100, and specimens were incubated for 45 minutes with the donkey-anti-goat-IgG-FITC-conjugated secondary antibody, which had been diluted at 1:200 in PBS containing 1% BSA (Jackson Immunoresearch Laboratories, West Grove, USA). Nuclear staining was done with DAPI obtained from Sigma-Aldrich (Singapore). The sections were then analyzed using an IX71 Olympus microscope (Tokyo, Japan). Images as shown in FIG. 17 were taken with a digital camera and processed using Photoshop 5.5 (Adobe Systems, San Jose, Calif.).

EXAMPLE 3

Reducing Surface Roughness by Coating Surfaces with Materials

Synthetic materials, cyanoacrylate and a polysulphone/PMMA solution, were used to coat surfaces of structures made by three-dimensional printing to reduce surface roughness. Using printed tubular structures as described above, the tubes were filled with cyanoacrylate and spun at 2500 RPM for 1 min. The tubes were then left to stand for 2 hours to allow the solvent in the cyanacrylate to evaporate. The tubes was sliced open with a scalpel and the internal surface of the pipe was examined with SEM (FIGS. 18A and 18B) and a profilometer scan (FIG. 19). From both the SEM micrograph and the profilometer scan, it was observed that surface roughness as well as the waviness of printed structure was significantly reduced by coating the surface with these materials.

Experiments to reduce surface roughness were also performed by coating collagen type 1 and fibronectin on the surface of a printed material in the shape of a tube. The material surface was fabricated using a hydrophobic Polyjet™ material (Contact angle-, Dataphysics™ OCA 30). The tube was filled with collagen (1.5% (wt)) and then drained. The collagen remaining on the printed surface was allowed to gel overnight in a $CO_2$ incubator at 37° C. Roughness of the surface was reduced by 3-4 µm using coatings of these materials.

An SEM study was performed to examine the coated surface of collagen. After the collagen was allowed to gel, the samples were rinsed with PBS, fixed in 2% glutaraldehyde in PBS (24 h, 4° C.), dehydrated in a series of ethanol and dried using critical point drier (Tousimis, Md., USA). The samples were sputtered with a platinum thin film with the JSM-7400F sputter device (Jeol, Japan) and the specimens were examined using JFC-1600 scanning electron microscope (Jeol, Japan). A similar experiment that follows the same protocol (modified for fibronectin) was performed with fibronectin.

This example shows that roughness of a surfaces can be reduced by coating surfaces with materials.

EXAMPLE 4

Fabrication of Structures Using a Two-Photon Lithography System

This example shows that structures of the invention can be fabricated using a two-photon lithography system.

A two-photon lithography system can be setup in a darkroom on, e.g., an 8'×5' optical table, with all modules controlled and synchronized with a computer. A three-dimensional image file is first loaded into the computer and processed into 1 µm thick two-dimensional cross-sectional slices. Each slice can be scanned and the focus of the laser can be progressively changed as each subsequent cross-section (frame) is drawn. An overview of the lithography system is provided by the flow chart in FIG. 5 and the diagram of the experimental setup in FIG. 6. The two-photon lithography system can be centered around a Coherent® Chameleon™ Ti-Sapphire laser, with peak power of 1.5 W (@ 800 nm, pulse repetition 80 MHZ, pulse width 120 fs), to provide photo energy for the polymerization of monomer. Beam from the laser is guided into a Scanlab™ scanner, piezoelectric scanner with a scan rate of 35 frames/s, to raster the desired two dimensional slices. A third dimension for the microfabricated process can be provided by modulating the focus point of the laser within the chemicals with a motorized objective lens. Finally, the beam may be steered onto the substrate with an Olympus BX51 microscope. With this setup, the device size may be limited to the field of view (FOV) of a microscope objective; FOV of a Nikon ELWD 20× lens a field of view of a circle of 150 µm in diameter has been achieved. To increase the FOV, a motorized stage was used to stitch devices together to form a much larger device.

Figure 7A:
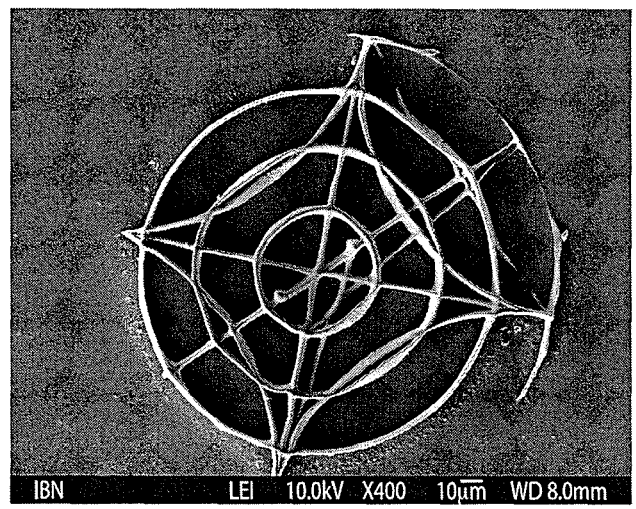
FIGS. 7A to 7D show SEM micrographs of structures fabricated by a two-photon lithography system according to another embodiment of invention.
Figure 7B:
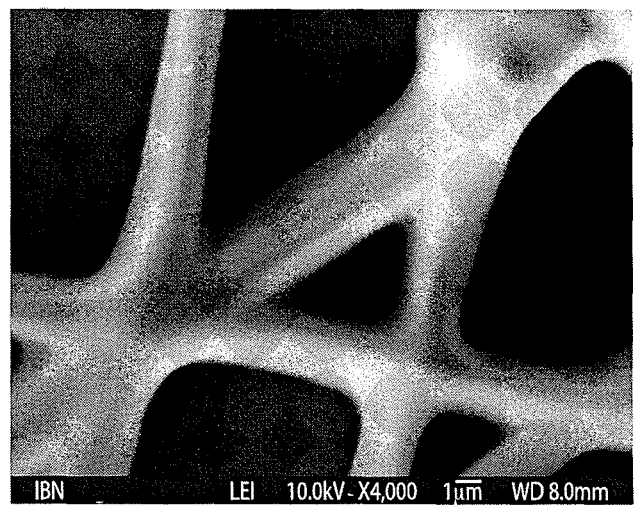
Figure 7C:
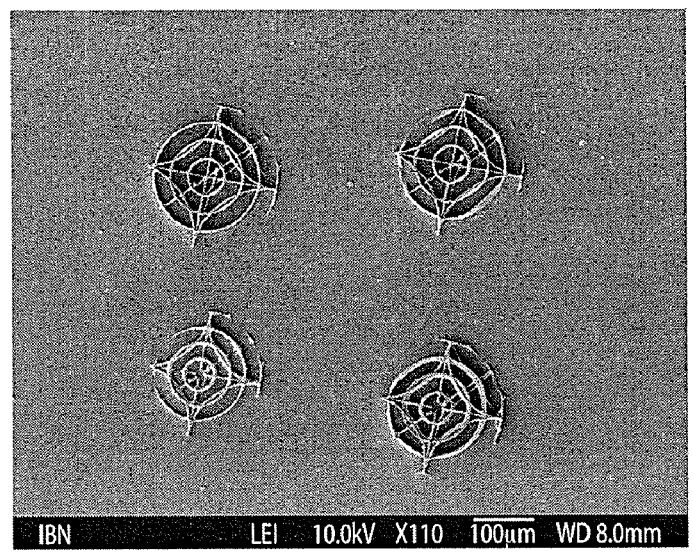
Figure 7D:
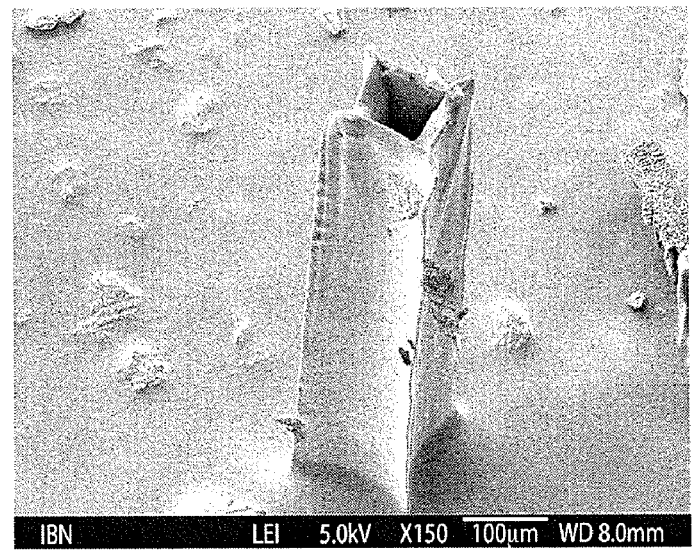

Porous three-dimensional devices can be fabricated using the system described above and by switching the shutter of the laser on and off. With this setup, complex three dimensional devices can be produced, e.g., as shown in FIGS. 7A-7D. FIG. 7A shows an SEM micrograph of two-dimensional structures having cross-sectional dimensions of less than 10 microns. FIG. 7B shows a magnified image of the structure shown in FIG. 7A, which illustrates the resolution of structures produced by a two-photon lithography system. FIG. 7C shows SEM micrograph of structures formed by stepping the motorized stage to form regular periodic features on a glass substrate. FIG. 7D shows an SEM micrograph of a 1.5 mm tall hollow tube having a wall thickness of about 2 to 5 microns, which was formed by the two-photon lithography system described above.

The process for fabricating high resolution devices may follows a three step process. First, the substrate which supports the structure is processed, then the substrate is scanned, and finally the scanned substrate is developed. The following provides a brief summary of the three step process:

1) Substrate preparation: In one embodiment, the substrate includes glass with a coating of ethoxylated bis phenol A dimethacrylate coated on glass.
   1) The glass substrate can be prepared by dipping in hot piranha for 1 min, rinsing and blowing them dry.
   2) Next, Renshape SL Y-C 9500 can be poured onto the glass slide and spun to coat the slide. The amount of chemical and spin rate may determine the height of the final coating.
2) Scanning: To expose the substrate, the flowing steps may be followed:
   1) Turn the laser from standby mode to operational mode.
   2) Tune the laser to 745 nm.
   3) Load the desired scan file into the computer.
   4) Place glass slide on to the stage of the microscope
   5) Adjust the focus of the laser onto the interface of the glass and RenShape SL Y-C 9500 chemical interface.
   6) Turn the shutter of the laser on and start the scan program.
   7) Once the scanning is done turn off the laser shutter and remove glass slide.
3) Develop: The unpolymerized chemical on the glass slide may be removed from the surface through an alcohol wash and rinse cycle.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article for use as a template for cell growth, comprising:
  a structure formed by a multi-photon lithographic process and comprising a photocurable polymer, the structure comprising at least one wall defining a cavity; and
  a plurality of pores having a cross-sectional dimension of less than 40 microns formed in at least a portion of the wall and permeating the wall, thereby enabling exchange of a component between a portion interior to the cavity and a portion exterior to the cavity,
  wherein at least a portion of the structure comprises a cell-adhering substance and at least a portion of the structure comprises a cell-inhibiting substance, and
  wherein the structure is constructed and arranged for use as a template for cell growth.

2. An article as in claim 1, wherein the plurality of pores have a cross-sectional dimension of less than or equal to 20 microns.

3. An article as in claim 1, wherein the plurality of pores have a cross-sectional dimension of less than or equal to 1 micron.

4. An article as in claim 1, wherein at least a portion of the wall has a thickness of less than 30 microns.

5. An article as in claim 1, wherein the cavity has an inner diameter of less than 300 microns.

6. An article as in claim 1, wherein the article is formed by a process comprising two-photon lithography.

7. An article as in claim 1, wherein the plurality of pores and the structure are fabricated by the same process.

8. An article as in claim 1, wherein the structure comprises a first cavity portion having a first inner diameter and a second cavity portion contiguous with the first cavity portion and having a second inner diameter.

9. An article as in claim 8, wherein the ratio of the first inner diameter to the second inner diameter is greater than 10:1.

10. An article as in claim 1, wherein the structure comprises a first substance that induces growth of a first cell type, and a second substance that induces growth of a second cell type.

11. An article as in claim 10, wherein at least a portion of the structure is modified with the first substance that induces growth of the first cell type, the article further comprising a substructure positioned within at least a portion of the cavity of the structure, the substructure including at least one portion modified with the second substance that induces growth of the second cell type, wherein the ratio between an inner diameter of the structure to an inner diameter of the substructure is greater than 10:1.

12. An article as in claim 11, wherein the substructure comprises a wall defining a cavity.

13. An article as in claim 12, wherein the wall of the substructure comprises a plurality of pores formed in at least a portion of the wall and permeating the wall, thereby enabling exchange of a component between a portion interior to the cavity of the substructure and a portion exterior to the cavity of the substructure.

14. An article as in claim 13, wherein the portion exterior to the cavity of the substructure comprises the portion interior to the cavity of the structure.

15. An article as in claim 1, wherein the structure comprises overlapping pores having a total pore size formed by the overlapping pores of less than 40 microns.

16. An article as in claim 1, wherein the structure is adapted to allow cell growth within the pores of the structure.

17. An article as in claim 1, wherein the article is a template for growing an artificial tissue or organ.

18. An article as in claim 17, wherein the artificial tissue or organ is selected from the group consisting of tissues or organs of the circulatory system, tissues or organs of the blood vessel system, tissues or organs of the digestive track, tissues or organs of the gut-associated glands, tissues or organs of the respiratory system, or tissues or organs of the urinary system.

19. An article as in claim 1, wherein the photocurable polymer comprises a crosslinking density that is varied within different portions of the structure.

20. An article as in claim 1, wherein the structure comprises an elastic material.

21. An article as in claim 1, wherein the photocurable polymer comprises an acrylate-based photopolymer.

22. An article as in claim 1, wherein the photocurable polymer comprises pentaerythritol triacrylate.

23. An article as in claim 1, wherein the photocurable polymer comprises an organic-inorganic hybrid material.

24. An article for use as a template for cell growth, comprising:

a structure formed by a multi-photon lithographic process and comprising a photocurable polymer, the structure comprising at least one wall defining a cavity, the cavity having an inner diameter of less than 300 microns; and a plurality of pores formed in at least a portion of the wall and permeating the wall, thereby enabling exchange of a component between a portion interior to the cavity and a portion exterior to the cavity, wherein at least a portion of the structure comprises a cell-adhering substance and at least a portion of the structure comprises a cell-inhibiting substance, and wherein the structure is constructed and arranged for use as a template for cell growth.

* * * * *